US008808683B2

(12) United States Patent
Rossmanith et al.

(10) Patent No.: US 8,808,683 B2
(45) Date of Patent: Aug. 19, 2014

(54) **GENETICALLY MODIFIED BACTERIUM OF THE SPECIES *LISTERIA MONOCYTOGENES***

(75) Inventors: Peter Rossmanith, Gaaden (AT); Karin Fruehwirth, Aspang (AT); Martin Wagner, Vienna (AT); Sabine Fuchs, Kirchstetten (AT)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 13/701,142

(22) PCT Filed: Apr. 29, 2011

(86) PCT No.: PCT/EP2011/002147
§ 371 (c)(1),
(2), (4) Date: Nov. 30, 2012

(87) PCT Pub. No.: WO2011/150999
PCT Pub. Date: Dec. 8, 2011

(65) Prior Publication Data

US 2013/0137100 A1 May 30, 2013

(30) Foreign Application Priority Data

Jun. 2, 2010 (EP) .................................... 10005731

(51) Int. Cl.
*A61K 39/02* (2006.01)
*A01N 63/00* (2006.01)
*C07H 21/02* (2006.01)

(52) U.S. Cl.
USPC ..... 424/93.2; 424/234.1; 424/93.1; 424/93.4; 536/23.1; 536/24.3; 536/24.32; 536/25.32

(58) Field of Classification Search
USPC ........... 424/93.1, 93.2, 93.4; 435/4, 6.1, 6.11, 435/6.12; 536/23.1, 24.3, 24.32, 25.32
See application file for complete search history.

(56) References Cited

U.S. PATENT DOCUMENTS

2010/0184210 A1 7/2010 Rossmanith et al.

FOREIGN PATENT DOCUMENTS

WO WO-2008 017097 2/2008

OTHER PUBLICATIONS

Rossmanith, P., et al. Research in Microbiology, vol. 157, pp. 763-771, 2006.*
Milohanic, E., et al. Molecular Microbiology, vol. 47, No. 6, pp. 1613-1625, 2003.*
Long, F., et al. Diagnostic Microbiology and Infectious Disease, vol. 62, pp. 374-381, 2008.*
Abdulmawjood, A. et al., "Two methods for construction of internal amplification controls for the detection of *Escherichia coli* O157 by polymerase chain reaction," Molecular and Cellular Probes, 2002, vol. 16, pp. 335-339.
Böckmann, R. et al., "Specific binding of the *Listeria monocytogenes* transcriptional regulator PrfA to target sequences requires additional factor(s) and is influenced by iron," Molecular Microbiology, 1996, vol. 22, No. 4, pp. 643-653.
Border, P. M. et al., "Detection of *Listeria* species and *Listeria monocytogenes* using polymerase chain reaction," Letters in Applied Microbiology, 1990, vol. 11, pp. 158-162.
Brehm-Stecher, B. et al., "Sample Preparation: The Forgotten Beginning," Journal of Food Protection, Aug. 2009, vol. 72, No. 8, pp. 1774-1789.

Bubert, A. et al., "Detection and Differentiation of *Listeria* spp, by a single reaction based on multiplex PCR," Applied and Environmental Microbiology, Oct. 1999, pp. 4688-4692.

D'Agostino, M. et al., "A Validated PCR-based method to detect *Listeria monocytogenes* using raw milk as food model—Towards an International Standard," Journal of Food Protection, 2004, vol. 67, No. 8, pp. 1646-1655.
Di Pasquale, S. et al., "Comparison of different concentration methods for the detection of hepatitis A virus and calicivirus from bottled natural mineral waters," Journal of Virological Methods, 2010, vol. 165, pp. 57-63.
Dickneite, C. et al., "Differential interaction of the transcription factor PrfA and the PrfA-activation factor (Paf) of *Listeria monocytogenes* with target sequences," Molecular Microbiology, 1988, vol. 27, No. 5, pp. 915-928.
Dreier, J. et al., "Use of bacteriophage MS2 as an Internal Control in viral Reverse Transcription-PCR Assays," Journal of Clinical Microbiology, Sep. 2005, pp. 4551-4557.
Earle, M. J. et al., "Ionic liquids. Green solvents for the future," Pure Appl. Chem., 2000, vol. 72, No. 7, pp. 1391-1398.

English Translation of Wasserscheid, P. et al., "Ionic liquids—New "Solutions" for Transition Metal Catalysis," 2000.

Glaser, P. et al., "Comparative Genomics of *Listeria* Species," Science, 2001, vol. 249, pp. 849-852.
Hagiwara, R. et al., "Room temperature ionic liquids of alkylimidazolium cations and fluoroanions," Journal of Fluorine Chemistry, 2000, vol. 105, pp. 221-227.
Hatefi, Y. et al., "Solubilization of particulate proteins and nonelectrolytes by chaotropic agents," Biochemistry, 1969, vol. 62, pp. 1130-1135.
Hoorfar, J. et al., "Letter to the Editor—Diagnostic PCR: Making Internal Amplification Control Mandatory," Letters in Applied Microbiology, 2003, vol. 38, pp. 79-80.
Hoorfar, J. et al., "Practical considerations in design of internal amplification controls for diagnosis of PCR assays," Journal of Clinical Microbiology, May 2004, pp. 1863-1868.
Kaltenboeck, B. et al., "Advances in Real-Time PCR: Application to Clinical Laboratory Diagnostics," Advances in Clinical Chemistry, 2005, vol. 40. pp. 215-259.
Lauer, P. et al., "Construction, Characterization, and Use of Two *Listeria monocytogenes* Site-Specific Phage Integration Vectors," Journal of Bacteriology, Aug. 2002, pp. 4177-4186.

(Continued)

*Primary Examiner* — Rodney P Swartz
(74) *Attorney, Agent, or Firm* — Millen, White, Zelano & Branigan, P.C.

(57) ABSTRACT

The present invention relates to a genetically modified bacterium of the species *Listeria monocytogenes*, wherein the genomic locus of the transcriptional factor PrfA has been deleted, characterized in that it comprises on genomic level an artificial sequence that acts as internal amplification control, the use of this bacterium as well as a method for detecting and determining qualitatively and/or quantitatively the occurrence of wild type *Listeria monocytogenes* in a sample suspected to be contaminated with said micro-organism and a kit.

16 Claims, 2 Drawing Sheets

(56) References Cited

OTHER PUBLICATIONS

Figure 1:
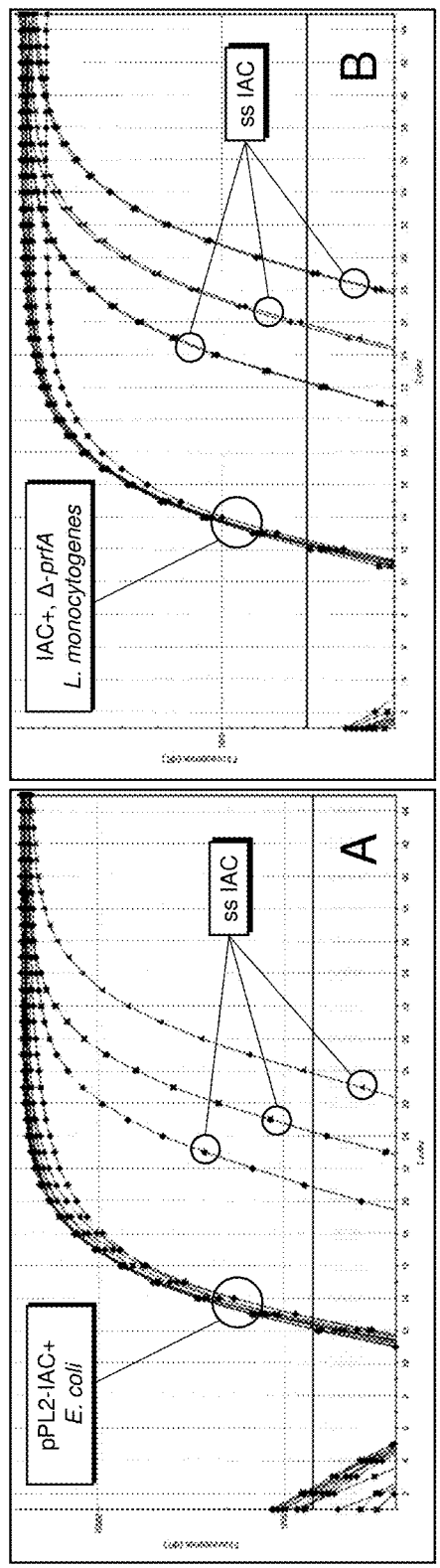

Lee, L. G. et al., "Allelic discrimination by nick-translation PCR with fluorogenic probes," Nucleic Acids Research, 1993, vol. 21, No. 16, pp. 3761-3766.

Leimeister-Wächter, M. et al., "Identification of a gene that positively regulates expression of listeriolysin, the major virulence factor of *Listeria monocytogenes*," Proc. Natl. Acad. Sci, Nov. 1990, vol. 87, pp. 8336-8340.

Mattison, K. et al., "The feline calicivirus as a sample process control for the detection of food and waterborne RNA viruses," International Journal of Food Microbiology, 2009, vol. 132, pp. 73-77.

Mester, P. et al., "Use of Ionic Liquid-Based Extraction for Recovery of *Salmonella* Typhimurium and *Listeria monocytogenes* from food matrices," Journal of Food Protection, 2010, vol. 21, No. 4, pp. 680-687.

Murphy, N. M. et al., "Construction and evaluation of a microbiological positive process internal control for PCR-based examination of food samples for *Listeria monocytogenes* and *Salmonella enterica*," International Journal of Food Microbiology, 2007, vol. 120, pp. 110-119.

Nelson, K. E. et al., "Whole genome comparisons of serotype 4b and 1/2a strains of the food-borne pathogen *Listeria monocytogenese* reveal new insights into the core genome components of this species," Nucleic Acids Research, 2004, vol. 32, No. 8, pp. 2386-2395.

Park, S. F. et al., "High-efficiencey transformation of *Listeria monocytogenes* by electoporation of penicillin-treated cells," Gene, 1990, vol. 94, pp. 129-132.

Rossmanith, P. et al. "Detection of *Listeria monocytogenes* in food using a combined enrichment/real-time PCR method targeting the prfa gene," Research in Microbiology, 2006, vol. 157, pp. 763-771.

Rossmanith, P. et al., "Development of matrix lysis for concentration of gram positive bacteria from food and blood," Journal of Microbiological Methods, 2007, vol. 69, pp. 501-511.

Rossmanith, P. et al., "Proof of concept for recombinant cellular controls in quantitative molecular pathogen detection," Applied and Environmental Microbiology, Apr. 2011, pp. 2531-2533.

Rossmanith, P. et al., "The challenge to quantify *Listeria monocytogens*—a model leading to new aspects in molecular biological food pathogen detection," Journal of Applied Microbiology, 2010, vol. 110, pp. 605-617.

Sambrook, J. et al., "Molecular Cloning: A Laboratory Manual, $2^{nd}$ Edition," 1989.

Scortti, M. et al., "The PrfA virulence regulon," Microbes and Infention, 2007, vol. 9, pp. 1197-1207.

Sheldon, R., "Catalytic reactions in ionic liquids," Chem. Commun., 2001, pp. 2399-2407.

Tyagi, S. et al., "Molecular Beacons: Probes that Fluoresce upon Hybridization," Nature Biotechnology, Mar. 1995, vol. 14, pp. 303-308.

Welton, T., "Room-Temperature Ionic Liquids. Solvents for Synthesis and Catalysis," Chem. Rev., 1999, vol. 99, pp. 2071-2083.

\* cited by examiner

GENETICALLY MODIFIED BACTERIUM OF THE SPECIES *LISTERIA MONOCYTOGENES*

SEQUENCE LISTING

The instant application contains a Sequence Listing which has been submitted electronically in ASCII format and is hereby incorporated by reference in its entirety. Said ASCII copy, created on Mar. 7, 2014, is named MERCK-4009_SL.txt and is 13,603 bytes in size.

The present invention relates to a genetically modified bacterium of the species *Listeria monocytogenes*, wherein the genomic locus of the transcriptional factor PrfA has been deleted, characterised in that it comprises on genomic level an artificial sequence that acts as internal amplification control, the use of this bacterium as well as a method for detecting and determining qualitatively and/or quantitatively the occurrence of wild type *Listeria monocytogenes* in a sample suspected to be contaminated with said micro-organism and a kit.

BACKGROUND OF THE INVENTION

*Listeria monocytogenes* is a pathogenic gram-positive bacterium. Causing Listeriosis it is one of the most virulent food borne pathogens.

The detection of pathogens in samples like food samples or clinical samples like blood, tissue or feces is becoming increasingly important. However, in order to clearly identify and optionally to quantify the cells comprised in a sample reliable methods for their detection and quantification have to be provided.

Since the first implementation of polymerase chain reaction (PCR) this molecular biological tool has been developed to a method providing many opportunities for improved detection of micro-organisms.

An important prerequisite for PCR based methods to become internationally recognized standard is the internal amplification control (IAC). An IAC is a non-target DNA sequence present in the same sample tube, which is co-amplified simultaneously with the target sequence. In a PCR without an IAC, a negative result is not definite as it can mean that there was no target sequence present but also that the amplification reaction was inhibited by various factors. Therefore the European Standardization Committee in collaboration with the International Standard Organisation (ISO) proposed a general guideline for diagnostic PCR that requires the presence of an IAC (ISO/DIS 22174).

The IAC should be competitive using the same primer binding sites as the target PCR and clearly distinguishable from the target DNA amplicons by means of length and fluorescence wavelength of the used probe dye in real-time PCR. In summary the characteristics of the control should be as close to the characteristics of the target nevertheless ensuring negligible interference on target detection.

The implementation of an IAC to PCR assays ensures the reliability of negative results; however, this is only true for the enzymatic reaction facilitating target amplification in PCR and for the quantitative and confirmative detection reaction based on the use of fluorescent probes in real-time PCR. However, preliminary methodical steps such as sample preparation and DNA-isolation/purification from the sample matrix are not covered by this kind of control and if at all, checked by external controls. This does not allow for control of single samples and thus negative results imply the possibility of false verification of the pathogen status of the investigated samples, e.g. food.

Therefore an internal sample process control (ISPC) is necessary which should cover all methodical steps which are necessary for reliable quantitative detection of pathogens with conventional or real-time PCR.

For detection of food and waterborne RNA viruses the use of Feline Calcivirus and the bacteriophage MS2 as internal controls has been reported (Mattison et al. (2009) Int. J. Food Microbiol. 132, 73-77; Di et al. (2010) J. Virol. Methods 165, 57-63; Dreier et al. (2005) J. Clin. Microbiol. 43, 4551-4557).

Murphy et al. (2007, Int. J. Food Microbiol. 120, 110-119) discloses a bacterial internal sample process control for the detection of *Listeria monocytogenes* and *Salmonella enterica*. This control is based on a recombinant *E. coli* strain including fragments of the green fluorescence gene (gfp) and the iroB gene of *S. enterica*. The control was not used for quantitative purposes and the underlying gram negative *E. coli* strain will exhibit different characteristics during sample preparation compared to *L. monocytogenes*.

Consequently, there is a need for new reliable methods allowing the detection and quantification of the pathogen *Listeria monocytogenes* by real-time PCR in contaminated samples.

Unexpectedly, it has been found that this problem can be solved by using an IAC+, Δ-prfA *L. monocytogenes* EGDe strain as internal process control covering the whole detection process.

DESCRIPTION OF THE INVENTION

A first aspect of the present invention is, therefore, a genetically modified bacterium of the species *Listeria monocytogenes*, wherein the genomic locus of the transcriptional factor PrfA has been deleted, characterised in that it comprises on genomic level an artificial sequence that acts as internal amplification control (IAC).

A genetically modified bacterium of the species *Listeria monocytogenes* means a *Listeria monocytogenes* species resulting from altering its genetic material using genetic engineering techniques. Genetic modification comprises the insertion and/or deletion of genes. The deletion of the prfA gene can e.g. be accomplished as disclosed in Bockmann et al. (1996) Mol. Microbiol. 22, 643-653.

The genomic locus of the transcriptional factor PrfA means the nucleic acid sequence encoding for the protein PrfA. This is a sequence of 705 base pairs (Leimeister-Wächter et al., 1990; Proc Natl Acad Sci USA, 87, 8336-40; Glaser et al., 2001; Science, 294, 849-52). The gene is located within the chromosomal region around the listeriolysin gene (lisA) of *L. monocytogenes* (Genel D: 987031; available at the world-wide-web URL ncbi.nlm.nih.gov/gene/987031). Information concerning the transcriptional factor PrfA is also given in Scortti et al. (2007) Microbes and Infection 9, 1196-1207, which is hereby incorporated by reference. PrfA controls the expression of key virulence determinants of *Listeria monocytogenes*. PrfA is a 237-residue protein of 27 kDa. The deletion of the genomic locus of the transcriptional factor PrfA renders the mutant non-pathogen.

According to the present invention internal amplification control (IAC) means an artificial nucleic acid sequence present in the sample tube during PCR reaction and co-amplified with a certain target sequence as defined by Hoorfar et al. (2003) Lett. Appl. Microbiol. 38, 79-80. The presence of an IAC allows to determine false-negative results. The IAC sequence may be any polynucleotide sequence. The size of this sequence may vary dependent on the specific PCR assay and reaction conditions thereof.

The IAC sequence is preferably a single-copy nucleotide sequence, i.e. a nucleotide sequence present only once in the haploid genome of a *Listeria monocytogenes* bacterium.

Preferably, the IAC sequence is a sequence not occurring in *Listeria monocytogenes* or any other species to be expected as naturally occurring within a sample to be investigated, or in the sample matrix itself.

Preferably, the IAC sequence comprises primer binding sequences at the 5' and 3' ends.

According to the present invention it is preferred that the IAC is a competitive IAC, i.e. the IAC of the genetically modified *Listeria monocytogenes* and the target sequence prfA of the wild type *Listeria monocytogenes* are amplified with one common set of primers under the same conditions and in the same PCR tube during real time PCR. Therefore, the primer binding sequences of the IAC are particularly preferably identical to the primer binding sequences of the genomic prfA locus of wild type *Listeria monocytogenes*.

In a very particularly preferred embodiment of the present invention the artificial IAC sequence is the 100 bp sequence according to SEQ ID NO: 1: 5'-GAT ACA GAA ACA TCG GTT GGC GTA TTC GAA ATG TCC GTT CGG TTG GCG CTA TGA AGA GAT ACG CGG TGG AAC CTG GAA CCT GAT GGC ATC AAG ATT ACA C-3'.

This IAC sequence is disclosed in Rossmanith et al. (2006) Res. Microbiol. 157, 763-771. According to the present invention IAC sequences of more than 80% homology to SEQ ID NO: 1 can be used. Preferably, the sequence homology is more than 90%, more preferably more than 95%.

According to the present invention a genetically modified *Listeria monocytogenes* EGDe strain as specified above is preferred.

The *Listeria monocytogenes* EGDe strain is a *Listeria monocytogenes* serovar ½a clinical preparation. This strain is the most widespread model organism in scientific use (GenBank: AL591978; Glaser et al. (2001) Science 294 (5543), 849-52).

A further aspect of the present invention is a genetically modified *Listeria monocytogenes* EGDe strain, wherein the genomic locus of the transcriptional factor PrfA has been deleted, comprising the internal amplification control sequence (IAC) of SEQ ID NO:1 as deposited at the DSMZ (Deutsche Sammlung von Mikroorganismen and Zellkulturen GmbH, Braunschweig) as *Listeria monocytogenes* ΔprfA/+IAC under DSM 23639 on May 20, 2010.

The genetically modified bacterium of the species *Listeria monocytogenes* according to the present invention meets the requirements given for a reliable internal sample process control. It is as closely related to wild-type *Listeria monocytogenes* as possible. It does not interfere with the main detection reaction by means of real-time PCR and the performance of the underlying chemical reaction for the detection of the control is equal to the main reaction. Additionally, the application of *Listeria monocytogenes* cells as ISPC permit to cover the whole progression of the necessary methods included in food pathogen detection from sample preparation to detection using real-time PCR.

Another aspect of the present invention is the use of genetically modified *Listeria monocytogenes* as specified above for detecting and determining qualitatively and/or quantitatively the occurrence of wild type *Listeria monocytogenes* in a sample suspected to be contaminated with said micro-organism.

Preferably, the sample is a food sample, a body fluid, in particular blood, plasma or serum, water or a tissue sample.

Exemplary samples include, but are not limited to, food e.g. milk of cows, ewes, nanny goats, mares, donkeys, camels, yak, water buffalo and reindeer, milk products, meat of beef, goat, lamb, mutton, pork, frog legs, veal, rodents, horse, kangaroo, poultry, including chicken, turkey, duck, goose, pigeon or dove, ostrich, emu, seafood, including finfish such as salmon and tilapia, and shellfish such as molluscs and crustaceans and snails, meat products, plant products, seeds, cereals from grasses, including maize, wheat, rice, barley, sorghum, and millet, cereals from non-grasses, including buckwheat, amaranth, and quinoa, legumes, including beans, peanuts, peas, and lentils, nuts, including almonds, walnuts, and pine nuts, oilseeds, including sunflower, rape and sesame, vegetables like root vegetables, including potatoes, cassava and turnips, leaf vegetables, including amaranth, spinach and kale, sea vegetables, including dulse, kombu, and dabberlocks, stem vegetables, including bamboo shoots, nopales, and asparagus, inflorescence vegetables, including globe artichokes, broccoli, and daylilies, and fruit vegetables, including pumpkin, okra and eggplant, fruits, herbs and spices, whole blood, urine, sputum, saliva, amniotic fluid, plasma, serum, pulmonary lavage and tissues, including but not limited to, liver, spleen, kidney, lung, intestine, brain, heart, muscle, pancreas and the like. The skilled artisan will appreciate that lysates, extracts or (homogenized) material obtained from any of the above exemplary samples or mixtures of said exemplary samples or compositions comprising one or more of said exemplary samples are also samples within the scope of the invention.

Particularly preferred is a food sample.

The food sample is preferably a milk product, preferably milk, in particular raw milk, milk powder, yoghurt, cheese or ice cream, a fish product, preferably raw fish, a meat product, preferably raw meat, meat rinse or sausages, salad rinse, chocolate, egg or egg products, like mayonnaise.

Particularly preferred food samples used in the method according to the present invention are samples which are usually known to comprise potentially pathogenic *Listeria monocytogenes*, e.g. cheese.

Preferably, the genetically modified *Listeria monocytogenes* as specified above is used as internal sample process control (ISPC) for a real-time PCR based assay.

According to the present invention an ISPC is a model organism added to the original sample prior to sample preparation. An ISPC provides a measure for the efficiency of the whole analytical chain from sample preparation to target molecule detection and covers all methodical steps which are necessary for reliable quantitative detection of pathogens with conventional or real-time PCR.

A further aspect of the present invention is a method for detecting and determining the occurrence of wild type *Listeria monocytogenes* in a sample suspected to be contaminated with said pathogenic micro-organism, comprising the steps:

(a) adding to said sample a predefined amount of cells of the genetically modified *Listeria monocytogenes* bacterium as specified above,
(b) incubating the sample with an extraction solution,
(c) isolating the DNA by standard methods;
(d) applying real-time PCR, thereby using (i) primers specific for the genomic prfA locus of wild type *Listeria monocytogenes* and the IAC sequence of genetically modified *Listeria monocytogenes* as specified above; and (ii) a fluorescent labelled oligonucleotide probe that is able to specifically hybridize with said prfA locus and a fluorescent labelled oligonucleotide probe that is able to specifically hybridize with said IAC sequence,
(e) determining qualitatively and/or quantitatively fluorescent signals generated by step (d), and (f) determining and/or calculating from step (e) the presence and/or the amount of the wild type *Listeria monocytogenes* cells in the original sample suspected to be contaminated with said micro-organism.

In step (a) a predefined amount of cells of the genetically modified *Listeria monocytogenes* bacterium as specified above is added to the sample. The amount added to the sample depends on the sample size. Preferably, an amount of 25 to 100000 CFU (colony forming units) of the genetically modified *Listeria monocytogenes* is added to a sample of e.g. 25 g. Particularly preferred is an amount of 100 to 5000 CFU per 25 g.

Colony forming unit (CFU) is a measure of viable cells in a sample. It can be determined by culture methods, e.g. by evenly spreading the sample on a bacterial culture gel. Incubation at suitable culture conditions results in the formation of colonies. The number of the colonies represents the number of colony forming units in the sample. Alternatively the cell count is determinable by microscopic count of fluorescent stained cells, e.g. using the Live/Dead® BacLight™ Bacterial Viability Kit (Molecular Probes, Willow Creek, Oreg., USA) or compareable commercial methods.

The extraction solution used in step (b) is an aqueous solution or a buffer solution. It typically has a pH value greater than 5 and lower than 9, preferably greater than 6 and lower than 8, more preferably between 6.5 and 7.5. The extraction solution may additionally comprise up to 20% of one or more water-miscible organic solvents.

The buffer which may be used in the method of the present invention is preferably selected from the group of phosphate buffer, phosphate buffered saline buffer (PBS), 2-amino-2-hydroxymethyl-1,3-propanediol (TRIS) buffer, TRIS buffered saline buffer (TBS) and TRIS/EDTA (TE).

In one embodiment of the present invention the extraction solution further comprises $MgCl_2$ and/or an ionic liquid. The $MgCl_2$—if present—is typically present in concentrations between 0.05 and 3 M, preferably between 0.1 and 2 M, more preferably between 0.3 and 1 M.

In another embodiment of the present invention the extraction solution further comprises at least one chaotrope and at least one detergent.

The ionic liquid—if present—is typically present in concentrations between 0.5 and 20% by weight, preferably between 1 and 10% by weight, based on the weight of mixture. The ionic liquid can be one ionic liquid or a mixture of two or more ionic liquids. In a preferred embodiment, the extraction solution comprises either $MgCl_2$ or ionic liquid.

Ionic liquids used in the present invention are ionic species which consist of an organic cation and a generally inorganic anion. They do not contain any neutral molecules and usually have melting points below 373 K. Review articles on ionic liquids are, for example, R. Sheldon "Catalytic reactions in ionic liquids", *Chem. Commun.*, 2001, 2399-2407; M. J. Earle, K. R. Seddon "Ionic liquids. Green solvent for the future", *Pure Appl. Chem.*, 72 (2000), 1391-1398; P. Wasserscheid, W. Keim "Ionische Flüssigkeiten—neue Lösungen für die Übergangsmetallkatalyse" [Ionic Liquids—Novel Solutions for Transition-Metal Catalysis], *Angew. Chem.*, 112 (2000), 3926-3945; T. Welton "Room temperature ionic liquids. Solvents for synthesis and catalysis", *Chem. Rev.*, 92 (1999), 2071-2083 or R. Hagiwara, Ya. Ito "Room temperature ionic liquids of alkylimidazolium cations and fluoroanions", *J. Fluorine Chem.*, 105 (2000), 221-227).

In general, all ionic liquids of the general formula $K^+ A^-$ known to the person skilled in the art, in particular those which are miscible with water, are suitable in the method according to the invention.

If an ionic liquid or $MgCl_2$ is present, in a further preferred embodiment, the extraction solution comprises no detergent, that means no anionic, zwitterionic or non-ionic detergent like sodium dodecylsulfate, CHAPS, Lutensol AO-7, is added to the extraction solution.

The term "chaotrope" as used herein, refers to a substance that causes disorder in a protein or nucleic acid by, for example, but not limited to, altering the secondary, tertiary or quaternary structure of a protein or a nucleic acid while leaving the primary structure intact. Exemplary chaotropes include, but are not limited to, guanidine hydrochloride (Gu-HCl), guanidinium thiocyanate (GuSCN), sodium thiocyanate (KSCN), sodium iodide, sodium perchlorate, urea, and the like. Descriptions of chaotropes and chaotropic salts can be found in, for instance, in K. Hamaguchi et al. (Proc. Natl. Acad. Sci. (1962) 62:1129-1136)

As used herein, the term "detergent" refers to molecules having lipophilic as well as hydrophilic (i.e. amphiphilic) characteristics. A detergent according to the present invention may comprise, for instance, a fatty acid residue and a hydrophilic (e.g. anionic or cationic) part.

Furthermore, it is possible to add to the extraction solution one or more additional substances like destabilizing agents or biopolymer degrading enzymes which help to degrade substances present in specific samples. One example is the addition of starch degrading enzymes for food sample comprising high amounts of collagen and/or starch.

The incubation is typically performed at temperatures between 18° C. and 50° C., preferably between 25° C. and 45° C., more preferably between 30° C. and 42° C.

The sample is typically incubated with the extraction solution for a time between 10 minutes and 6 hours, preferably between 20 minutes and 1 hour.

In order to facilitate the dissolution of the sample, said sample can be, for instance, homogenized using a stomacher prior its incubation with the extraction solution. The dissolution is further supported and/or accelerated when the mixture is agitated during the incubation.

Further extraction methods can for example be found in Brehm-Stecher et al. (2009) Journal of Food Protection 72: 1774-1789.

According to the present invention, the DNA of the bacterial material is isolated in step (c). Various methods known in the art may be employed to extract DNA, e.g. the methods disclosed in Sambrook et al. (1989) Molecular cloning: a laboratory manual, 2nd ed. Cold Spring Harbor Laboratory Press, Cold Spring Harbor, N.Y.

In general, DNA extraction comprises cell lysis and DNA purification by either precipitation or specific binding on various substrates e.g. silica.

Cell lysis may be accomplished by standard methods, e.g. by enzymatic methods, bead methods, sonication, detergent methods or combinations thereof. Preferably, detergent methods are employed.

Suitable enzymes for enzymatic cell lysis are, e.g., lysozyme, lysostaphin, zymolase, cellulase, mutanolysin, glycanases, proteases, mannase.

Beads suitable for cell disruption are of glass, ceramic, zirconium, or steel. After the addition of beads to the cells agitation by stirring or shaking of the mix is applied. Agitation can for example be applied by a common laboratory vortex mixer or in a specially designed clamp.

According to the present invention, a further method for cell lysis is sonication. This method involves ultrasound application (typically 20-50 kHz) onto the sample.

Detergent-based cell lysis results in the disruption of the lipid barrier surrounding cells. Suitable detergents may be chosen from non-ionic, zwitterionic and ionic detergents, e.g. CHAPS, Triton® X or TWEEN®. Preferably, ionic detergents are used. An example for a suitable ionic detergents is SDS.

In addition to the choice of detergent, other important considerations for optimal cell lysis include the buffer, pH, ionic strength and temperature: The lysis solution typically has a pH value greater than 5 and lower than 9, preferably greater than 6 and lower than 8, more preferably between 6.5 and 7.5.

The buffer which may be used is preferably selected from the group of phosphate buffer, phosphate buffered saline buffer (PBS), 2-amino-2-hydroxymethyl-1,3-propanediol (TRIS) buffer, TRIS buffered saline buffer (TBS) and TRIS/EDTA (TE).

Optionally, one or more chelating agents can be added to the lysis solution to sequester divalent cations. Suitable chelators are, e.g., EDTA (ethylenediamine tetraacetic acid), EGTA (ethylene glycol tetraacetic acid) or ethylenediamine. Preferably, EDTA is used.

The above mentioned cell lysis methods are typically followed by centrifugation in order to separate the DNA from the cellular material. A skilled person can easily determine the parameters for centrifugation. Typically, centrifugation is carried out as disclosed in Sambrook et al. (1989) Molecular cloning: a laboratory manual, 2nd ed. Cold Spring Harbor Laboratory Press, Cold Spring Harbor, N.Y.

After cell lysis the DNA is usually precipitated by adding an alcohol, preferably ethanol or isopropanol.

Additionally, the DNA can be provided in a form which is suitable for amplification using a commercially available DNA isolation kit, such as the NucleoSpin® tissue kit and the support protocol for Gram-positive bacteria (Machery-Nagel, Düren, Germany) or the Nexttec® kit for genomic DNA from bacteria (Nexttec GmbH Biotechnologie, Leverkusen, Germany).

In a further embodiment of the present invention the bacterial material is separated prior to DNA isolation in step (c). This further step is particularly preferred since it allows for achieving a higher concentration of DNA in the resulting PCR sample. Separation of the bacterial material can be accomplished by any known method, like centrifugation, filtration, dielectrophoresis and ultrasound or affinity binding, e.g. using antibodies, lectins, viral binding proteins, aptamers or antimicrobial peptides (AMP) which are preferably immobilized on beads. Preferably, the cells are isolated by filtration or centrifugation, most preferred by centrifugation. Filtration of the extracted sample is in particular required when the complex sample comprises material which is hardly or not extractable with the method of the present invention. Typically these materials comprise starch and/or fibres. However, the preferred method for isolation the cells from the extraction mixture is centrifugation.

The incubation step may—depending on the sample matrix—be repeated once or several times, e.g. twice, three times, four times, five times or ten times. Between these incubation steps the bacterial material and the remnant sample matrix may be separated from the supernatant by e.g. centrifugation.

After the separation of the bacterial material the cells are preferably washed with water, a buffer solution and/or detergent comprising solutions. The wash step may be repeated several times.

In step (d) PCR, preferably real-time PCR is applied. Real-time PCR is a method for detecting and measuring products generated during each cycle of a PCR, which are proportionate to the amount of template nucleic acid prior to the start of PCR. The information obtained, such as an amplification curve, can be used to quantitate the initial amounts of template nucleic acid sequence.

The detection is preferably based on monitoring fluorescence at every cycle at a set temperature. Fluorescence is usually monitored using an optical device to collect the data at specific excitation and emission wavelengths for the particular fluorescent dye present in the sample. The cycle at which the fluorescence from a sample crosses the threshold for detection of fluorescence above background is called the cycle threshold, Ct, and allows the quantification of the starting template.

The PCR conditions are not particularly restricted but optimal conditions may be selected for each PCR apparatus. For example, the following conditions may be used:

Thermal denaturation of double-stranded DNA to single-stranded DNA: Heating is generally made at about 90-98° C., preferably at about 92-96° C., generally for about 3 seconds to 1 minute, preferably for about 30 seconds to 1 minute.

Annealing: Heating is made generally at about 40-70° C., preferably at 55-65° C., generally for about 5 seconds to 2 minutes, preferably for about 30 seconds to 90 seconds.

DNA elongation reaction: Heating is made generally at about 60-75° C., preferably at about 70-74° C., generally for about 10 seconds to 3 minutes, preferably for about 30 seconds to 2 minutes.

Mg ion concentration in the reaction liquid: Generally about 1-5 mM, preferably about 1.5-3.5 mM.

This reaction is typically carried out in about 20-50 cycles, preferably in about 45 cycles, whereby the target DNA can be amplified to a detectable level.

Any commercial real-time PCR apparatus can be used.

According to step (d)(i) of the method of the present invention primers specific for the genomic prfA locus of wild type *Listeria monocytogenes* and the IAC sequence of genetically modified *Listeria monocytogenes* as defined above are used.

In general, the term "primer" refers to a short nucleic acid molecule, such as a DNA oligonucleotide of 9 nucleotides or more in length, that is complementary to a section along a strand of the target nucleic acid, i.e. the genomic prfA locus and the IAC sequence, wherein the purpose of the primer is to initiate the nucleic acid replication of a longer nucleic acid along the strand. According to the present invention primers of 15 to 40 nucleotides are preferred. In the present invention the term "primers" is used for the primer pair, flanking the targeted sequence to be amplified.

Preferably, the primers used in step (d)(i) are Lip1 and Lip2.

```
The sequence of Lip1 is:
                                    (SEQ ID NO: 2)
5'-GAT ACA GAA ACA TCG GTT GGC-3'
and the sequence of Lip2 is:
                                    (SEQ ID NO: 3)
5'-GTG TAA TCT TGA TGC CAT CAG G-3'.
```

According to step (d)(ii) of the method of the present invention a fluorescent labelled oligonucleotide probe that is able to specifically hybridize with said prfA locus and a fluorescent labelled oligonucleotide probe that is able to specifically hybridize with said IAC sequence are used.

According to the present invention the term "specifically hybridize" means to detectably and specifically bind. Polynucleotides, oligonucleotides and fragments thereof selectively hybridize to nucleic acid strands under hybridization conditions that minimize appreciable amounts of detectable binding to non-specific nucleic acids.

A fluorescent labelled oligonucleotide is an oligonucleotide exhibiting a typically covalently attached fluorophor. A fluorophor is a chemical compound, which when excited by exposure to a particular wavelength of light, emits light (fluoresces), for example at a different wavelength of light.

Preferably, the oligonucleotide probes that are able to specifically hybridize with said prfA locus and said IAC sequence exhibit different fluorophors emitting light of different wavelengths. This allows the detection of one probe independently from the other.

The fluorescent labelled probes typically used for real time PCR are e.g. LightCycler (hybridisation) probes, molecular beacons or hydrolysis probes (also called TaqMan® probes). Preferably, hydrolysis probes are used.

LightCycler probes utilize the technique of fluorescence resonance energy transfer (FRET). For this method two different oligonucleotide probes bound to a FRET donor and a FRET acceptor, respectively, are used for each target sequence. These probes bind side by side to the target sequence, bringing the fluorophors in proximity.

Molecular beacons (Tyagi et al., Nat. Biotechnol. 14:303-8, 1996) are oligonucleotide probes bound to a reporter fluorophor and a quencher. The nucleotides on the 5' end are complementary to the nucleotides on the 3' end, forming a stem loop structure. Because of the proximity of the fluorophor and the quencher no fluorescence is observed. Hybridization of the probe with the target sequence during real-time PCR leads to an increase in the reporter-quencher distance resulting in fluorescence of the reporter.

Preferably, hydrolysis probes (TaqMan® probes) are used (Lee et al., Nucleic Acids Res. 21:3761-6, 1993). These probes utilize as well the technique of fluorescence resonance energy transfer (FRET). The probes exhibit a fluorescent reporter at one end and a quencher of fluorescence at the opposite end. Because of the close proximity of the reporter to the quencher detection of the reporter fluorescence is suppressed. During the annealing stage of the PCR both primers and the probe anneal to the DNA target. Polymerization of a new DNA strand leads to the degradation of the probe by the 5'-3' exonuclease activity of the polymerase and physical separation of the fluorescent reporter from the quencher, resulting in an increase in fluorescence. Fluorescence can be detected and measured in the real-time PCR thermocycler, and its geometric increase corresponding to exponential increase of the product is used to determine the threshold cycle (Ct) in each reaction (see below).

Exemplary reporters include, but are not limited to: 6-carboxyfluorescein; carboxyfluorescein (FAM); boron dipyrromethene difluoride (BODIPY); acridine, stilbene, 6-carboxy-fluorescein (HEX), TET (Tetramethyl fluorescein), 6-carboxy-X-rhodamine (ROX), Rhodamine-6G, Texas Red, 2',7'-dimethoxy-4',5'-dichloro-6-carboxyfluorescein (JOE), Cy®3, Cy®5, VIC® (Applied Biosystems), LC Red 640, LC Red 705, Texas Red, Yakima Yellow®, as well as derivatives thereof. Preferably, a reporter selected from FAM and HEX is used in the present invention.

Exemplary quenchers include, but are not limited to Black Hole Quenchers (WO 01/86001 A1) as BHQ1™ and BHQ2™, MGB (Minor-groove-binder, EP 0819133 B1), N,N,N',N'-tetramethyl-6-carboxyrhodamine (TAMRA), Eclipse® Dark Quencher, DABCYL, DABSYL, DDQ I and DDQ II According to the present invention, preferably used quenchers are MGB or BHQ1™.

A person skilled in the art can easily chose a suitable reporter-quencher combination. Typically, the absorption spectrum of the quencher needs to have a good overlap with the emission spectrum of the reporter in order to allow for optimal quenching.

Preferably, the fluorescent labelled probe hybridizing with the IAC sequence of step (d)(ii) is pLucLm4 (SEQ ID NO:4) as disclosed in Rossmanith et al. (2006) Res. Microbiol. 157, 763-771. The fluorescent labelled probe hybridizing with the prfA locus is preferably LipProbe (SEQ ID NO:5).

The fluorescent labelled probe pLucLm4 exhibits preferably HEX as reporter fluorophor and BHQ1™ as quencher.

The fluorescent labelled probe LipProbe exhibits preferably FAM as reporter and MGB as quencher.

According to the present invention the fluorescent signals generated by step (d) are qualitatively and/or quantitatively determined in step (e).

The detection is preferably based on monitoring fluorescence at every cycle at a set temperature. Fluorescence is usually monitored using an optical device to collect the data at specific excitation and emission wavelengths for the particular fluorophors present in the sample.

In step (f) the presence and/or the amount of wild type *Listeria monocytogenes* cells in the original sample suspected to be contaminated with said micro-organism is determined and/or calculated from step (e).

The presence of wild type *Listeria monocytogenes* cells in the original sample is typically determined by qualitatively determining the fluorescent signals in step (e).

The amount of wild type *Listeria monocytogenes* cells in the original sample is typically calculated comprising the following steps:

Calculating the initial amount of DNA by means of DNA copies of the genetically modified *Listeria monocytogenes* and wild-type *Listeria monocytogenes* by using the Ct method (Threshold method) based on the respective fluorescence signal after real-time PCR amplification. The threshold method is based on the comparsion of the respective signal of the investigated sample with a calibration standard (Kaltenböck et al. (2005), Advances in Clinical Chemistry 40: 219-259).

Calculating the loss during the analytical procedure (comprising sample preparation, DNA purification and isolation and real-time PCR according to steps (b), (c) and (d) of the method of the present invention) based on the known value of initial cells of genetically modified *Listeria monocytogenes* within the sample and the value of cells as obtained by the Ct method after real-time PCR.

Calculating the number of wild type *Listeria monocytogenes* cells present in the sample suspected to be contaminated with said microorganism based on the calculated loss of genetically modified *Listeria monocytogenes* cells during the analytical procedure.

The method of the present invention is advantageous since the use of *Listeria monocytogenes* as an internal sample process control (ISPC) for molecular biological pathogen detection provides most similarity with the target organism and therefore most applicability for bacterial pathogen detection. Even a nearly related species such as *Listeria* innocua would lead to a non-competitive internal control requiring a second primer pair during real-time PCR. The simple use of a DNA based ISPC derived from an existing IAC, from the very beginning of the detection process, would as well not fulfil the prerequisite of most similarity of control and target. Besides, most of the DNA would get lost during the various methodical steps before PCR detection.

A further aspect of the present invention is a kit for use in an assay for detecting and determining wild type *Listeria monocytogenes* in a sample suspected to be contaminated with said micro-organism, comprising at least in one or more packages (i) genetically modified *Listeria monocytogenes* as specified above;

(ii) the primers specific for the genomic prfA locus of wild type *Listeria monocytogenes* and the IAC sequence of genetically modified *Listeria monocytogenes* as specified above; and (iii) a fluorescent labelled oligonucleotide probe that is able to specifically hybridize with said prfA locus and a fluorescent labelled oligonucleotide probe that is able to specifically hybridize with said IAC sequence.

Preferably, the primers of the kit are Lip1 (SEQ ID NO:2) and Lip2 (SEQ ID NO:3).

The fluorescent labelled probes are preferably pLucLm4 (SEQ ID NO:4) for detecting the IAC sequence and LipProbe (SEQ ID NO:5) for detecting the prfA locus.

According to the present invention the kit may additionally comprise an extraction solution.

Another aspect of the present invention is a method for manufacturing a genetically modified *Listeria monocytogenes* bacterium as specified above comprising the steps:

(a) deleting the genomic locus of the transcriptional factor PrfA of the bacterial species *Listeria monocytogenes,*

(b) cloning of a vector comprising an IAC, (c) transforming the vector of step (b) into the bacterial species of step (a).

The deletion of the genomic locus of PrfA according to step (a) is accomplished by techniques known in the art and can for example be accomplished as disclosed in Böckmann et al. (1996) Mol. Microbiol. 22, 643-653. In principle, a knock-out plasmid is constructed. This plasmid is transformed into *Listeria monocytogenes* cells. Crossing-over results in the excision of the prfA gene. The resulting organism is also referred to as Δ-prfA *Listeria monocytogenes.*

Optimal culture conditions for *Listeria monocytogenes* bacteria can easily be determined by a skilled person. Typically, the bacteria are grown in TSB-Y (Trypton soya broth with yeast extract) at 37° C. with aeration.

In step (b) a vector comprising the IAC is produced.

Adequate amounts of the IAC sequence for cloning are typically produced by amplification of the sequence by conventional PCR (Rossmanith et al. (2006) Res. Microbiol. 157, 763-771). The primers used for PCR typically comprise restriction sites for special restriction enzymes allowing for later integration into the vector. For an IAC sequence according to SEQ ID NO:1 the modified primers LipBam (SEQ ID NO:6) and LipSal (SEQ ID NO:7) comprising the restriction sites BamHI and SalI, respectively, are preferably used.

```
The sequence of LipBam is:
                                        (SEQ ID NO: 6)
5'GCG CGG ATC CGA TAC AGA AAC ATC GGT TGG C'3.
```

```
The sequence of LipSal is
                                        (SEQ ID NO: 7)
5'GCG CGT CGA CGT GTA ATC TTG ATG CCA TCA GG'3.
```

After purification of the amplification product restriction digestion, dephosphorylation and ligation with a suitable integration vector are performed.

Restriction digestion is typically performed by incubation of the amplification product with commercially available restriction enzymes corresponding to the restriction sites of the primers used for PCR. Preferably, BamHI and SalI are used.

Dephosphorylation of the IAC fragments can be accomplished by incubation with a suitable phosphatase, e.g. Fast AP™ Thermosensitive Alkaline Phosphatase (Fermentas). A suitable integration vector can easily be chosen by a skilled person. The vector comprises a gene sequence giving resistance to an antibiotic that the intended recipient strain of bacteria is sensitive to (e.g. chloramphenicol) in order to allow for later selection of positive clones. Preferably, a phage insertion vector, e.g. pPL1 or pPL2 as disclosed in Lauer et al. (2002) J. Bacteriol. 184, 4177-4186 is used. The phage insertion vector pPL2 (6123 bp) is particularly preferred since it provides stable single copy insertion into the genome of *Listeria monocytogenes.*

Adequate amounts of the insertion vector can be produced by amplifying the vector in a bacterium, e.g. in *E. coli* TOP10F', and subsequent isolation, restriction digestion and dephosphorylation as described above. Typically, the restriction sites can be found in a multiple cloning site (MCS) of the vector.

Ligation is typically performed by the addition of a DNA ligase, e.g. T4 DNA ligase available from Fermentas.

The resulting vector is transformed into a suitable bacterium, e.g. *E. coli* TOP10F' for amplification and for the selection of positive clones. This selection is typically accomplished by plating the bacteria on a medium comprising the above mentioned antibiotic.

In step (c) the vector of step (b) is transferred into the *Listeria monocytogenes* cells of step (a). The transformation can be carried out using the various methods well-known in the state of the art. Examples are transformation by heat shock or electroporation. Preferably, transformation is effectuated by electroporation.

Transformation by heat shock is accomplished by chilling the cells in the presence of divalent cations such as $Ca^{2+}$ (in $CaCl_2$) or $Rb^{2+}$ ($RbCl_2$) preparing the cell membrane to become permeable to plasmid DNA. Cells are incubated on ice with the DNA and then briefly heat shocked (typically at 41 to 43° C. for 30 to 120 seconds).

For electroporation the cells are briefly shocked with an electric field of 10-25 kV/cm. Preferably, electroporation is accomplished according to Park et al. (1990) Gene 94, 129-132.

The resulting organism can be tested upon successful cloning. Successful insertion of the vector into the Δ-prfA *Listeria monocytogenes* genome can be tested by amplification of the 499 bp fragment by PCR (according to Lauer et al. (2002) J. Bacteriol. 184, 4177-4186) and by sequencing.

Single copy insertion of the IAC into the genome of Δ-prfA *Listeria monocytogenes* can be verified by comparison of the genomic DNA amounts of transformed *Listeria monocytogenes* measured by UV/VIS spectroscopy with the data after real-time PCR in comparison to wild-type data, based on the known size of the *Listeria* genome (Nelson et al. (2004) Nucleic Acids Res. 32, 2386-2395).

The present invention is further illustrated by the following figures and examples, however, without being restricted thereto.

FIG. 1. Confirmation of pPL2-IAC, *E. coli* and IAC+, Δ-prfA *L. monocytogenes* EGDe (according to Examples 1.4 and 1.6). (A) Real-time PCR amplification of pPL2-IAC, *E. coli* clones after transformation and plasmid isolation targeting the artificial IAC within the plasmid. The amplification plots on the left side include the plasmid preparation as target. The amplification plots on the right side (ss IAC) represent the calibration function (Efficiency.: 96.8%; Rsq: 0.999). (B) Real-time PCR amplification of IAC+, Δ-prfA *L. monocytogenes* EGDe clones targeting the artificial IAC within the genome for confirmation of integration of the vector pPL2-IAC into the *Listeria* genome (Eff.: 96.0%; Rsq.: 0.999). The amplification plots on the left side include genomic DNA of four IAC+, Δ-prfA *L. monocytogenes* EGDe clones as target.

Figure 2:
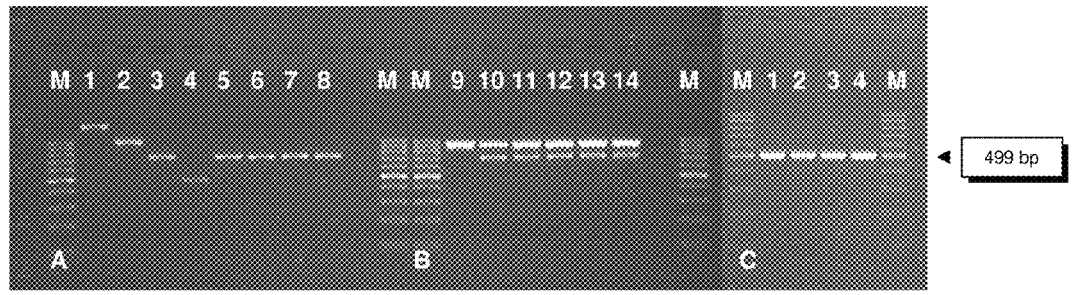

FIG. 2. Confirmation of positive integration of pPL2-IAC into the *Listeria* genome and confirmation of the resulting IAC+, Δ-prfA *L. monocytogenes* EGDe strain by conventional PCR (according to Example 1.6.). (A) Agarose gel of the cloned strains, confirmed as *L. monocytogenes*. M, Marker; 1, *L. ivanovii, L. seeligeri* and *L. welshimeri;* 2, *L. innocua;* 3, *L. monocytogenes;* 4, *L. grayi;* 5-8, Four IAC+, Δ-prfA *L. monocytogenes* EGDe clones. (B) Confirmation of the IAC+, Δ-prfA *L. monocytogenes* EGDe amplifying the 16S rRNA gene specific for all *Listeria* spp. and the hly gene specific for *L. monocytogenes.* 9, L. spp.; 10, *L. monocytogenes;* 11-14, Four IAC+, Δ-prfA *L. monocytogenes* EGDe clones. (C) Confirmation of the integration of the pPL2-IAC into the genome of the Δ-prfA *L. monocytogenes* EGDe strain. 1-4, Four IAC+, Δ-prfA *L. monocytogenes* EGDe clones. The resulting 499 bp fragment after PCR indicates integration. PCR products are separated in a 1% agarose gel and stained with ethidium bromide.

The entire disclosures of all applications, patents, and publications cited above and below are hereby incorporated by reference.

1. Examples

The following examples describe practical applications of the invention.

1.1. Bacterial Strains and Culture Conditions.

*L. monocytogenes* EGDe (½a, internal number 2964) is part of the collection of bacterial strains at the Institute of Milk Hygiene, Milk Technology and Food Science, Department of Veterinary Public Health and Food Science, University of Veterinary Medicine, Vienna, Austria (IMML). Δ-prfA *L. monocytogenes* EGDe (½a) is part of the collection of bacterial strains at the Department of Microbiology, Theodor Boveri Institute, University of Würzburg, Würzburg, Germany. Electro-competent *E. coli* TOP10F' are available at Invitrogen (Carlsbad, Calif., USA). All bacterial strains are maintained at −80° C. using MicroBank™ technology (Pro-Lab Diagnostics, Richmont Hill, Canada).

Measurement of the optical density of bacterial cultures is performed at 600 nm ($OD_{600}$) in duplicate with an HP 8452 spectrophotometer (Hewlett Packard, Paolo Alto, Calif., USA). Selective plating of *L. monocytogenes* EGDe wt and IAC+, Δ-prfA *L. monocytogenes* EGDe is performed on RAPID' L.mono (Bio-Rad laboratories GmbH, Munchen, Germany), OCLA (Oxoid Chromogenic *Listeria* agar; Oxoid, Hampshire, UK), PALCAM (Solabia Biokar Diagnostics, Pantin Cedex, France) and blood agar (Biomerieux, Marcy l'Etoile, France) whether by streaking 100 µlbacterial culture to the plates or by loop technique.

Enumeration of bacterial suspensions is performed using the plate count method or the Live/Dead® BacLight™ Bacterial Viability Kit (Molecular Probes, Willow Creek, Oreg., USA) according to manufacturer's instructions.

1.2. Oligonucleotides, Plasmids and Enzymatic Reactions.

The sequences of oligonucleotides and plasmids are presented in Table 1. Primers for conventional and real-time PCR and the HEX-labelled probe pLuclm4 are available from MWG Biotech (Ebersberg, Germany); the MGB-modified Lip-probe from Applied Biosystems (Foster City, Calif., USA). The artificial 100 bp target for the IAC is synthesized by VBC Genomics Vienna, Austria). The pPL2 phage insertion vector according to Lauer et al. (2002) J. Bacteriol. 184, 4177-4186.

TABLE 1

Oligonucleotide and primer sequences and organisms

| | | Sequence/Label | Ref./Source |
|---|---|---|---|
| Oligonucleotides | | | |
| Lip 1 | Forward primer[a] | 5'-GAT ACA GAA ACA TCG GTT GGC-3' | D'Agostino et al., 2004 |
| Lip 2 | Reverse primer[a] | 5'-GTG TAA TCT TGA TGC CAT CAG G-3' | D'Agostino et al., 2004 |
| Lip Bam | Forward primer[b] | 5'GCG CGG ATC CGA TAC AGA AAC ATC GGT TGG C'3 | SEQ ID NO: 6 |
| Lip Sal | Reverse primer[c] | 5'GCG CGT CGA CGT GTA ATC TTG ATG CCA TCA GG'3 | SEQ ID NO: 7 |
| LipProbe | Probe binding prfA locus[a] | FAM-CAG GAT TAA AAG TTG ACC GCA-MGB | Rossmanith et al., 2006, SEQ ID NO: 5 |
| pLucLm 4 | Probe binding artificial target | HEX-TTC GAA ATG TCC GTT CGG TTG GC-BHQ1 | Rossmanith et al., 2006, SEQ ID NO: 4 |
| IAC | Artificial target | 5'-GAT ACA GAA ACA TCG GTT GGC GTA TTC GAA ATG TCC GTT CGG TTG GCG CTA TGA AGA GAT ACG CGG TGG AAC CTG GAA CCT GAT GGC ATC AAG ATT ACA C-3' | Rossmanith et al., 2006, SEQ ID NO: 1 |

TABLE 1-continued Oligonucleotide and primer sequences and organisms

| | | Sequence/Label | Ref./Source |
|---|---|---|---|
| NC 16 | Confirmation of pPL2 insertion | 5'-GTC AAA ACA TAC GCT CTT ATC-3' | Lauer et al., 2002 |
| PL 95 | Confirmation of pPL2 insertion | 5'-ACA TAA TCA GTC CAA AGT AGA TGC-3' | Lauer et al., 2002 |
| Sequ. 1 (NC 16) | Confirmation of pPL2 insertion | Sequence included in Table 1A | This work |
| Sequ. 2 (PL 95) | Confirmation of pPL2 insertion | Sequence included in Table 1A | This work |

| Species/Plasmid | Strain | | |
|---|---|---|---|
| *L. monocytogenes* wt | EGDe (1/2a) | Wild type strain detected by prfA real-time PCR | IMML[d] Strain Nr. 2964 |
| *L. monocytogenes* Δtarget | EGDe (1/2a) ΔprfA | *L. monocytogenes* EGDe strain with total deletion of the prfA locus | Böckmann et al., 1996 |
| *E. coli* TOP10F' | — | Chemically competent *E. coli* | Invitrogen |
| pPL2 Phage insertion vector | *L. monocytogenes* specific | PSA intergration site. Stable single copy integrants: ~10$^{-4}$/donor cell. | Lauer et al., 2002 |

[a]Specific to *L. monocytogenes* wt
[b]Primer containing Bam HI restriction site.
[c]Primer containing Sal I restriction site.
[d]IMML: Institute of Milk Hygiene, Milk Technology and Food Science, University of Veterinary Medicine Table 1 discloses SEQ ID NOS 2-3,6-7,5,4,1 and 8-9, respectively, in order of appearance.

TABLE 1A

Sequences and blast reports of the analysis of the amplification products of the PCR according to Lauer et al., 2002

| Name/Primer | Blast report | Reference[a] | Sequence[b] |
|---|---|---|---|
| Sequence 1 Clone 1/NC16 | Identities = 210/210 (100%), Gaps = 0/210 (0%), Strand = Plus/Plus Identities = 267/268 (99%), Gaps = 1/268 (0%), Strand = Plus/Plus | emb AJ417449.2 Shuttle integration vector pPL2 emb AL591978.1 *Listeria monocytogenes* strain EGD, complete genome, segment 6/12 | ANNNANNNACGTATCCAGTTCGATTCATGGACCGAGATGAC AACGAACTAACAGACCTAACCCAAACCTTCCCATTAACGAAG CGTAACTAGGTCAAAAGACACCCGAAAAAGAAAAAATGCAT AACTTAAAGAAAACCATTGACAAACAAGCGATTTAAACATA AAATGGTATTTGGCTGTTGAAAAGACAGTGCCATTTGTCCTG ATAGCTCAGCTGGATAGAGCAACGGCCTTCTAAGCCGTCGGT CGGGGGTTCGAATCCCTCTCAGGACGTTAAATAGTAATGTAA AGAAATCTCTAAAACGTTGAAAAGCCTTGATATTAAAGGGCG GATGAATGTTTTGGAGTTTTTTTTATATCGTATAATACCCGTT TTATTCCGTTGTTTTTGTGGCATTTGTGGTAAAATTTGTGGTA TTTTCATCTGTTTTTAGTGTGAAAAAAGCATCTACTTTGGACT GATTATGGTAAAACCACCAACTTGGAATGGATAAGGTCATCT CCATTGGAGAGAGTATGTGCACCCACTACTTACGGATGATTT AG |
| Sequence 1 Clone 1/NC16 | Identities = 210/210 (100%), Gaps = 0/210 (0%), Strand = Plus/Plus Identities = 261/261 (100%), Gaps = 0/261 (0%), Strand = Plus/Plus | emb AJ417449.2 Shuttle integration vector pPL2 emb AL591978.1 *Listeria monocytogenes* strain EGD, complete genome, segment 6/12 | GGNNNTGAAACGNNCNAGTTCGATTCATGGACCGAGATGAC AACGAACTAACAGACCTAACCCAAACCTTCCCATTAACGAAG CGTAACTAGGTCAAAAGACACCCGAAAAAGAAAAAATGCAA TAACTTAAAGAAAACCATTGACAAACAAGCGATTTAAACATA AAATGGTATTTGGCTGTTGAAAAGACAGTGCCATTTGTCCTG ATAGCTCAGCTGGATAGAGCAACGGCCTTCTAAGCCGTCGGT CGGGGGTTCGAATCCCTCTCAGGACGTTAAATAGTAATGTAA AGAAATCTCTAAAACGTTGAAAAGCCTTGATATTAAAGGGCG GATGAATGTTTTGGAGTTTTTTTTATATCGTATAATACCCGTT TTATTCCGTTGTTTTTGTGGCATTTGTGGTAAAATTTGTGGTA TTTTCATCTGTTTTTAGTGTGAAAAAAGCATCTACTTTGGACT GATTATGGTAAAACAACCTACTTGGGATGGTTAAGGGCACA TCCATTGGAGAGAGTATGTGTANCCTCTTTGGAGGACTGATG AGG |

TABLE 1A-continued

Sequences and blast reports of the analysis of the amplification products of the PCR according to Lauer et al., 2002

| Name/Primer | Blast report | Reference[a] | Sequence[b] |
|---|---|---|---|
| Sequence 1 Clone 1/NC16 | Identities = 209/210 (99%), Gaps = 1/210 (0%), Strand = Plus/Plus Identities = 267/268 (99%), Gaps = 1/268 (0%), Strand = Plus/Plus | emb AJ417449.2 Shuttle integration vector pPL2 emb AL591978.1 *Listeria monocytogenes* strain EGD, complete genome, segment 6/12 | NNAANNNGTATCCAGTTCGATTCATGGACCGAGATGACAAC GAACTAACAGACCTAACCCAAACCTTCCCATTAACGAAGCGT AACTAGGTCAAAAGACACCCGAAAAAGAAAAAATGCAATAA CTTAAAGAAAACCATTGACAAACAAGCGATTTAAACATAAA ATGGTATTTGGCTGTTGAAAAGACAGTGCCATTTGTCCTGAT AGCTCAGCTGGATAGAGCAACGGCCTTCTAAGCCGTCGGTCG GGGGTTCGAATCCCTCTCAGGACGTTAAATAGTAATGTAAAG AAATCTCTAAAACGTTGAAAAGCCTTGATATTAAAGGGCGGA TGAATGTTTTGGAGTTTTTTTTATATCGTATAATACCCGTTTT ATTCCGTTGTTTTTGTGGCATTTGTGGTAAAATTTGTGGTATT TTCATCTGTTTTTAGTGTGAAAAAAGCATCTACTTTGGCTGAT TATGGTAAATCCACCTACTTTGAATGGATAAGGTCATCTCCA TTGGAGAGAGTATGTGTATCTACTTTGTAGGGATGATGATGT ACCACCTAGGTTGGACTGAATAGGTCCCCCCTTCTTCGATTA AACAACGGGATAAAGTA |
| Sequence 1 Clone 1/NC16 | Identities = 211/211 (100%), Gaps = 0/211 (0%), Strand = Plus/Plus Identities = 266/268 (99%), Gaps = 2/268 (0%), Strand = Plus/Plus | emb AJ417449.2 Shuttle integration vector pPL2 emb AL591978.1 *Listeria monocytogenes* strain EGD, complete genome, segment 6/12 | NNNNTNNCNAAGTATCCAGTTCGATTCATGGACCGAGATGA CACGAACTAACAGACCTAACCCAAACCTTCCCATTAACGAAG CGTAACTAGGTCAAAAGACACCCGAAAAAGAAAAAATGCAA TAACTTAAAGAAAACCATTGACAAACAAGCGATTTAAACATA AAATGGTATTTGGCTGTTGAAAAGACAGTGCCATTTGTCCTG ATAGCTCAGCTGGATAGAGCAACGGCCTTCTAAGCCGTCGGT CGGGGGTTCGAATCCCTCTCAGGACGTTAAATAGTAATGTAA AGAAATCTCTAAAACGTTGAAAAGCCTTGATATTAAAGGGCG GATGAATGTTTTGGAGTTTTTTTATATCGTATAATACCCGTT TTATTCCGTTGTTTTTGTGGCATTTGTGGTAAAATTTGTGGTA TTTTCATCTGTTTTTAGTGTGAAAAAAGCATCTACTTTGGACT GATTATGTAAAACAACCTACTTTGGATGGATTAGGTAATATC TTTTTGACAGAGTATGTGTACCATCTTTTTAGGACTGATTATG TA |
| Sequence 1 Clone 1/PL95 | Identities = 172/176 (97%), Gaps = 3/176 (1%), Strand = Plus/Minus Identities = 300/302 (99%), Gaps = 0/302 (0%), Strand = Plus/Minus | emb AJ417449.2 Shuttle integration-vector pPL2 emb AL591978.1 *Listeria monocytogenes* strain EGD, complete genome, segment 6/12 | NNNNANNAAAAACGNATGAAATACCACAAATTTTACCACAA ATGCCACAAAAACAACGGAATAAAACGGGTATTATACGATA TAAAAAAAACTCCAAAACATTCATCCGCCCTTTAATATCAAG GCTTTTCAACGTTTTAAAGATTTCTTTACATTACTATTTAACG TCCTGAGAGGGATTCGAACCCCCGACCGACGGCTTAAAAGG CCGTTGCTCTATCCAGCTGAGCTATCAGGACAAATGGCACTG TCTTTTCAACAGCCAAATACCATTTTATGTTTAAATCGCTTGT TTGTCAATGGTTTTCTTTAAGTTATTGCATTTTTTCTTTTTCG GGTGTCTTTTGACCTATTTACGCTTCGTTAATGGGAAGGTTT GGGTTAGGTCTGTTAGTTCGTTGTCATCTCGGTCCATGAATC GAACTTGGATACCTTCTGGTGTTGAATCGATAAGAGCGTATG TTTTGAACAACCACCTACTTTGGACTGATTAGGTAA |
| Sequence 1 Clone 1/PL95 | Identities = 165/168 (98%), Gaps = 1/168 (0%), Strand = Plus/Minus Identities = 292/293 (99%), Gaps = 0/293 (0%), Strand = Plus/Minus | emb AJ417449.2 Shuttle integration vector pPL2 emb AL591978.1 *Listeria monocytogenes* strain EGD, complete genome, segment 6/12 | TNNTNNANACGATGACATACCACAAATTTTACCACAAATGCC ACAAAAACAACGGAATAAAACGGGTATTATACGATATAAAA AAAACTCCAAAACATTCATCCGCCCTTTAATATCAAGGCTTT TCAACGTTTTAAAGATTTCTTTACATTACTATTTAACGTCCTG AGAGGGATTCGAACCCCCGACCGACGGCTTAAAAGGCCGTT GCTCTATCCAGCTGAGCTATCAGGACAAATGGCACTGTCTTT TCAACAGCCAAATACCATTTTATGTTTAAATCGCTTGTTGTC AATGGTTTTCTTTAAGTTATTGCATTTTTTCTTTTTCGGGTGT CTTTTGACCTAGTTACGCTTCGTTAATGGGAAGGTTTGGGTT AGGTCTGTTAGTTCGTTGTCATCTCGGTCCATGAATCGAACT TGGATACCTTCTGGTGTTGAATCGATAAGAGCNNTGTTTTTT GTANACAAAACCTTTTACTTTGGACTGAATAAGGTACCCCCC CTTGTAAAGGTTTTATGTGAACCNCCCTTTGTAGAGTTAATTT GGAACCACCGAGGGGGGATTGATTAGGCCACCCTGCCTTTAA GTTCAGGTGGGCGACAN |
| Sequence 1 Clone 1/PL95 | Identities = 171/174 (98%), Gaps = 2/174 (1%), Strand = Plus/Minus Identities = 301/302 (99%), Gaps = 0/302 (0%), Strand = Plus/Minus | emb AJ417449.2 Shuttle integration vector pPL2 emb AL591978.1 *Listeria monocytogenes* strain EGD, complete genome, segment 6/12 | NNTTAGNTAAAACGATGAAATACCACAAATTTTACCACAAAT GCCACAAAAACAACGGAATAAAACGGGTATTATACGATATA AAAAAAACTCCAAAACATTCATCCGCCCTTTAATATCAAGGC TTTTCAACGTTTTAAAGATTTCTTTACATTACTATTTAACGTC CTGAGAGGGATTCGAACCCCCGACCGACGGCTTAAAAGGCC GTTGCTCTATCCAGCTGAGCTATCAGGACAAATGGCACTGTC TTTTCAACAGCCAAATACCATTTTATGTTTAAATCGCTTGTTT GTCAATGGTTTTCTTTAAGTTATTGCATTTTTTCTTTTTCGGG TGTCTTTTGACCTAGTTACGCTTCGTTAATGGGAAGGTTTGG GTTAGGTCTGTTAGTTCGTTGTCATCTCGGTCCATGAATCGA ACTTGGATACCTTCTGGTGTTGAATCGATAAGAGCGTATGTT TTTGACCAACCATCAACTTTGGACGGATTAGGTAACCTCCAT TTGAGAGAGTATATGTAACACCTATTTTGGGAGGTATGATGA AAAN |

TABLE 1A-continued

Sequences and blast reports of the analysis of the amplification products of the PCR according to Lauer et al., 2002

| Name/Primer | Blast report | Reference[a] | Sequence[b] |
|---|---|---|---|
| Sequence 1 Clone 1/PL95 | Identities = 167/168 (99%), Gaps = 1/168 (0%), Strand = Plus/Minus Identities = 300/302 (99%), Gaps = 0/302 (0%), Strand = Plus/Minus | emb AJ417449.2 Shuttle integration vector pPL2 emb AL591978.1 Listeria monocytogenes strain EGD, complete genome, segment 6/12 | TNNNNGTANAAANGATGAAATACCACAAATTTTACCACAAA TGCCACAAAAACAACGGAATAAAACGGGTATTATACGATAT AAAAAAAACTCCAAAACATTCATCCGCCCTTTAATATCAAGG CTTTTCAACGTTTTAGAGATTTCTTTACATTACTATTTAACGT CCTGAGAGGGATTCGAACCCCCGACCGACGGCTTAAAAGGC CGTTGCTCTATCCAGCTGAGCTATCAGGACAAATGGCACTGT CTTTTCAACAGCCAAATACCATTTTATGTTTAAATCGCTTGTT TGTCAATGGTTTTCTTTAAGTTATTGCATTTTTTCTTTTTCGG GTGTCTTTTGACCTAGTTACGCTTCGTTAATGGGAAGGTTTG GGTTAGGTCTGTTAGTTCGTTGTCATCTCGGTCCATGAATCG AACTTGGATACCTTCTGGTGTTGAATCGATAAAAGCGTATGT TTTGAAAAACCATCAACTTTGAACGGATTAGGTAACCTCCAT TTTGGAGAGA |

[a]Refered to by blast report
[b]As obtained by sequencing

Table 1A discloses SEQ ID NOS 10-17, respectively, in order of appearance.

Restriction digestion is performed using FastDigest® restriction enzymes BamHI and SalI available from Fermentas (Fermentas International Inc., Burlington, Canada) according to manufacturer's instructions. A total reaction volume of 20 μl is incubated for one hour at 37° C. Dephosphorylation of the vector and the IAC fragments before ligation is performed using FastAP™ Thermosensitive Alkaline Phosphatase (Fermentas) according to manufacturer's instructions for 30 min at 37° C. T4 DNA ligase (Fermentas) is used for ligation of the vector pPL2 and the artificial IAC fragment over night at 4° C.

Real-time PCR detection of L. monocytogenes by targeting a 274 bp fragment of the prfA gene is performed according to previously published format using the primers Lip1 and Lip2 and FAM-labelled Lip-probe (D'Agostino et al. (2004) J. Food Prot. 67, 1646-1655; Rossmanith et al. (2006) Res. Microbiol. 157, 763-771). Real-time PCR detection of the artificial IAC fragment is performed according to Rossmanith et al. (2006) using Lip1 and Lip2 and HEX-labelled pLucLm4.

The forward primer (Lip1:5'-GATACAGAAACATCGGT-TGGC-3') (SEQ ID NO: 2) and the reverse primer (Lip2:5'-GTGTAATCTTGATGCCATCAGG-3') (SEQ ID NO: 3) amplify a 274 bp fragment of the prfA gene. Two different TaqMan™ probe formats with increased melting temperature are used. The Lip-probe (5'-FAM-CAGGATTAAAAGT-TGACCGCA-MGB-3') (SEQ ID NO: 5) uses an MGB modification. The probe for the IAC of the assay (pLucLm 4: 5'-HEX-TTCGAAATGTCCGTTCGGTTGGC-BHQ1-3') (SEQ ID NO: 4) is HEX labelled. Primers and probe pLucLm 4 can be purchased at MWG Biotech (Ebersberg, Germany). The MGB-modified probe is purchased at Applied Biosystems.

Conventional PCR for confirmation of the insertion of pPL2-IAC into the Δ-prfA L. monocytogenes EGDe genome is performed using primers NC16 and PL95 (Lauer et al. (2002) J. Bacteriol. 184, 4177-4186). IAC+, Δ-prfA L. monocytogenes EGDe is identified as L. monocytogenes EGDe by amplifying the iap-locus of L. monocytogenes according to Bubert et al. (1999, Appl. Environ. Microbiol. 65, 4688-4692) and targeting the 16S rRNA gene specific for all Listeria spp. and the hly gene specific for L. monocytogenes according to Border et al. (1990, Lett. Appl. Microbiol. 11, 158-162).

Conventional and real-time PCR reactions are performed in an Mx3000p real-time PCR thermocycler (Stratagene, La Jolla, Calif., USA). The 25 μl volume contains 20 mM Tris-HCl, 50 mM KCl, 3.5 mM $MgCl_2$, 500 nM of each primer, 250 nM of each probe, 200 μM (each) of dATP, dTTP, dGTP and dCTP, 1.5 U of Platinum© Taq DNA polymerase (Invitrogen, Lofer, Austria) and 5 μl isolated DNA. Amplification following initial denaturation at 94° C. for 2 min is performed in 45 cycles, at 94° C. for 15 s, and 64° C. for 1 minute.

For the DNA standard for real-time PCR quantification one milliliter of a pure culture of L. monocytogenes strain EGDe is subjected to DNA isolation using the NucleoSpin© tissue kit and the support protocol for Gram-positive bacteria. The DNA concentration is measured fluorimetrically using a Hoefer DyNA Quant200 device (Pharmacia Biotech). The copy number of the prfA gene is determined by assuming that, based on the molecular weight of the genome of L. monocytogenes, 1 ng of DNA equals $3.1 \times 10^5$ copies of the entire genome, and that the prfA gene is a single-copy gene. The slope (s) of the standard curve is used for calculation of the PCR efficiency (E) with the following equation: $E=10^{-1/s}-1$ [21].

Real-time PCR results are expressed as bacterial cell equivalents (BCE). The copy number of the prfA gene and the IAC insert is determined by assuming that, based on the molecular weight of the genome of L. monocytogenes, 1 ng of DNA equalled $3.1 \times 10^5$ copies of the entire genome, and that the prfA gene and the IAC insert are a single-copy gene and a single copy insert within the genome respectively (Nelson et al. (2004) Nucleic Acids Res. 32, 2386-2395). All real-time PCR reactions are performed in duplicate except as noted otherwise.

PCR products of conventional PCR are separated in 1.5% agarose gels at 90 V for 25 min and stained with 0.5 μg/ml ethidium bromide (Sigma-Aldrich GmbH, Steinheim, Germany). GeneRuler 100 bp (MBI Fermentas, St. Leon-Rot, Germany) was used as a standard.

1.3. DNA Extraction and Measurement.

The genomic DNA of one milliliter overnight bacterial culture is extracted by using the NucleoSpin® tissue kit (Macherey—Nagel) and the support protocol for Gram-positive bacteria. Plasmid DNA for cloning experiments is extracted using the Quiagen Plasmid Midi Kit (Hilden, Germany) according to manufacturer's instructions. DNA concentration is analytically determined by fluorimetric measurement using a Hoefer DyNA Quant200 apparatus (Pharmacia Biotech, San Francisco, Calif., USA) and a 8452A Diode Array Spectrophotometer (Hewlett Packard, Palo Alto, Calif., USA).

1.4. Cloning of pPL2-IAC.

Adequate amounts of the IAC (IAC: 5-GAT ACA GAA ACA TCG GTT GGC GTA TTC GAA ATG TCC GTT CGG TTG GCG CTA TGA AGA GAT ACG CGG TGG AAC CTG GAA CCT GAT GGC ATC AAG ATT ACA C-3') (SEQ ID NO: 1) for cloning are produced by amplification of the 100 bp fragment by conventional PCR according to Rossmanith et al. (2006, Res. Microbiol. 157, 763-771) using the modified primers LipBam and LipSal containing the restriction sites BamHI and SalI. After purification of the amplification product using NucleoSpin® Extract II (Macherey-Nagel) restriction digestion and dephosphorylation are performed as described above, following ligation with the vector pPL2. Prior to ligation the phage integration vector pPL2 is transformed into *E. coli* TOP10F' by standard heat shock techniques (Sambrook et al. (1989) Molecular cloning: a laboratory manual, 2nd ed. Cold Spring Harbor Laboratory Press, Cold Spring Harbor, N.Y.) for amplification. The vector is extracted as described above and used for ligation after purification, restriction digestion and dephosphorylation. The resulting plasmid pPL2-IAC is then transformed into *E. coli* TOP10F' via heat-shock. pPL2-IAC positive clones are selected by plating on Luria-Bertani broth (LB; Oxoid) containing 25 µg/ml of chloramphenicol.

Single bacterial colonies are picked up and screened for positive transformation of *E. coli* with pPL2-IAC. Restriction digestion analysis results in two fragments of a length of ~6,000 bp and 100 bp corresponding to the lengths of vector and insert indicating transformation of pPL2-IAC into *E. coli*. Real-time PCR targeting the IAC using pLucLm4 results in amplification of the target, thus confirming the restriction digestion analysis (FIG. 1A).

1.5. Transformation of pPL2-IAC into Δ-prfA *L. Monocytogenes* EGDe.

Δ-prfA *L. monocytogenes* EGDe is transformed with pPL2-IAC using a modified electroporation protocol (Park et al. (1990) Gene 94, 129-132). Electro-competent Δ-prfA *L. monocytogenes* EGDe cells are prepared as follows: Cells are grown in brain heart infusion broth (BHI; Oxoid) containing 5 μg/ml penicillinG to an $OD_{600}$ of 0.3 at 37° C. Cells are harvested at 8000×g, 10 min at 4° C. and the pellet is washed twice in 1/10 vol. 3.5×SMHEM buffer (72 mM sucrose, 1 mM $MgCl_2$, and 2 mM HEPES). After resuspending the pellet in 1/100 vol. 3.5×SMHEM buffer 100 μl aliquots are stored at −80° C.

For electroporation 100 μl aliquots of electro-competent Δ-prfA *L. monocytogenes* EGDe are thawed on ice and mixed with 5 μl DNA suspension (~1 μg/reaction) containing pPL2-IAC. After incubation for one min on ice, electroporation is performed (100Ω, 50 μF, 1000 V) in a Gene Pulser Xcell™ electroporation system (Bio-Rad Laboratories, Inc, Hercules, Calif., USA). One milliliter of pre warmed BHI is added, the sample is incubated 6 h at 37° C. and subsequently plated on BHI agar containing 25 μg/ml of chloramphenicol. After 24-48 h incubation at 37° C. individual colonies are picked and screened for pPL2-IAC positive Δ-prfA *L. monocytogenes* EGDe clones.

1.6. Confirmation of IAC+, Δ-prfA *L. Monocytogenes* EGDe.

Four chloramphenicol screening positive clones of IAC+, Δ-prfA *L. monocytogenes* EGDe are confirmed by testing the presence of the IAC sequence in Δ-prfA *L. monocytogenes* EGDe. This is performed by amplifying the 100 bp fragment of the IAC using the probe pLucLm4. Genomic DNA from IAC+, Δ-prfA *L. monocytogenes* EGDe is subjected to real-time PCR resulting in positive amplification (FIG. 1B). The tested clones achieve a mean Ct-value of 11.5 (SD (standard deviation): 0.16) corresponding to a mean of $5.36\times10^7$ copies. The Δ-prfA status of the cloned strain is tested by real-time PCR using the probe Lip-probe hybridizing the 274 bp fragment of the prfA locus of the wild type *L. monocytogenes* resulting in no amplification.

Integration of the vector within the genome is tested with conventional PCR as described under paragraph 1.2. The resulting fragments after electrophoresis correspond to the proposed length of the amplification product of 499 bp (FIG. 2C). This indicates insertion of the vector into the *Listeria* genome as the primers NC16 and PL95 allow amplification across the attachment site $tRNA^{Arg}$-attBP' in *L. monocytogenes* serotype ½a resulting in a hybrid amplificate containing parts of the sequences of the vector (3') and of the *Listeria* genome (5').

Sequencing analysis of IAC+, Δ-prfA *L. monocytogenes* EGDe is performed using this hybrid PCR amplificate using primers NC16 and PL95. The obtained sequence is 100% identical with a 210 bp fragment of the shuttle integration vector pPL2 and 100% identical to a 261 bp fragment of *L. monocytogenes* including the proposed attachment site $tRNA^{Arg}$-attBP' (Strain EGDe, complete genome, segment 6/12; emb/AL591978.1). Confirmation testing of the resulting IAC+, Δ-prfA strain to be *L. monocytogenes* EGDe is additionally performed by conventional PCR as described under paragraph 1.2. The results are presented in FIGS. 2A and B. demonstrating matching fragment sizes for IAC+, Δ-prfA *L. monocytogenes* EGDe and the control *L. monocytogenes* EGDe for both PCR assays.

1.6. IAC+, Δ-prfA *L. monocytogenes* EGDe Sequencing.

PCR products from positive clones after amplification are purified using the NucleoSpin® Extract II Kit (Macherey-Nagel), following the manufacturer's instructions. Purified PCR products are submitted to Macrogen Inc. (Seoul, Korea) for DNA sequencing. Samples are sequenced on both strands using NC16 and PL95 primers on the cycle sequencing reaction.

The obtained sequences are analyzed and aligned using the BLAST server available at the National Center for Biotechnology Information website (available on the world-wide-web URL ncbi.nlm.nih.gov/BLAST/).

1.7. Quantitative Real-Time PCR for Confirmation of Single Copy Insertion of pPL2-IAC into the Genome of Δ-prfA *L. Monocytogenes* EGDe and Calibration Against *L. Monocytogenes* EGDe Wild Type Data.

Calibration standards of genomic IAC+, Δ-prfA *L. monocytogenes* EGDe DNA and *L. monocytogenes* EGDe wild type are compared using the prfA real-time PCR assay in a multiplex system with the probes pLucLm4 and Lip-probe. Based on the assumption that prfA is a single copy gene ten fold dilutions of both DNA targets are compared. The ten-fold dilutions are starting at $1.58\times10^6$ copies equalling 5 ng of genomic DNA as determined by fluorimetric and UV-VIS measurement. The results are presented in Table 3 and show good concordance of the Ct-values of both standard series. This also demonstrates comparable performance of both probes within the reactions. The underlying data result from duplicates repeated in four real-time PCR runs. For confirmation of these results the concentrations of cultures of IAC+, Δ-prfA *L. monocytogenes* EGDe are determined by viability staining and compared to real-time PCR results. The number of $3.2\times10^3$ (RSD.: 6.7%) BCE per sample as obtained by real-time PCR compares to $2.8\times10^3$ (RSD.: 25.0%) CFU per sample as determined by viable staining.

TABLE 3

Comparsion of Ct-values after real-time PCR derived from a ten-fold standard dilution of genomic DNA of *L. monocytogenes* EGDe wild type and the cloned EGDe Δ-prf; IAC+ strain demonstrating single copy insertion of pPL2-IACa into the genome of *L. monocytogenes* EGDe Δ-prfA.

| | Strain | | |
|---|---|---|---|
| | EGDe Δ-prfA, IAC+ | EGDe wt | EGDe wt against EGDe Δ-prfA, IAC+ background |
| Target | Monoplex PCR | | Duplex PCR |
| Copy Nr.[b] | Ct-values (SD)[c] | Ct-values (SD)[d] | Ct-values (SD)[d,e] |
| $1.58 \times 10^6$ | 16.8 (0.08) | 16.6 (0.11) | — |
| $1.58 \times 10^5$ | 20.1 (0.13) | 20.0 (0.02) | 19.9 (0.13) |
| $1.58 \times 10^4$ | 23.4 (0.14) | 23.1 (0.18) | 23.4 (0.26) |
| $1.58 \times 10^3$ | 26.8 (0.13) | 26.7 (0.06) | 26.7 (0.31) |
| $1.58 \times 10^2$ | 30.4 (0.07) | 30.1 (0.02) | 29.9 (0.68) |
| $1.58 \times 10^1$ | 33.8 (0.27) | 34.1 (0.91) | 33.4 (0.77) |

[a]Based on the assumption that prfA is a single copy gene.
[b]Dilution series derived from a solution containing 1 ng/µl genomic DNA representing $1.58 \times 10^6$ copies in 5 µl DNA template.
[c]prfA real-time PCR assay using HEX labelled pLucLM4 probe, amplifiying the artificial IAC sequence.
[d]prfA real-time PCR assay using FAM labelled Lip-probe, amplifiying 274 bp of the prfA locus sequence.
[e]Genomic DNA of *L. monocytogenes* EGDe against $1.58 \times 10^5$ copies background of the genome of the EGDe Δ-prfA, IAC+ strain in a multiplex reaction.

The influence of increasing amounts of genomic DNA derived from IAC+, Δ-prfA *L. monocytogenes* EGDe on the performance of the main reaction amplifying the prfA locus of the wild type strain and main bacterial target is investigated with multiplex real-time PCR. Using Lip-probe and pLucLm4, ten-fold dilutions of genomic *L. monocytogenes* EGDe wild type DNA starting at $1.58 \times 10^6$ copies to $1.58 \times 10^1$ are tested in an ascending as well as descending matrix against a background of ten-fold dilutions of $1.58 \times 10^6$ to $1.58 \times 10^1$ copies of genomic IAC+, Δ-prfA *L. monocytogenes* EGDe DNA. The resulting Ct values for all tested combinations deviate from the respective values as obtained by the monoplex experiments of the genomic standards of both strains with a mean standard deviation of 0.3 for all combinations of standard concentration. Exemplarily the resulting Ct-values for a tenfold dilution of genomic DNA of *L. monocytogenes* EGDe are presented in Table 3 against a background of $1.58 \times 10^5$ copies of IAC+, Δ-prfA *L. monocytogenes* EGDe.

1.8. Artificially and Naturally Contaminated Food Samples.

UHT milk for artificial contamination is purchased at local supermarkets and tested to be *L. monocytogenes* negative prior to inoculation performing real-time PCR targeting the prfA locus of *L. monocytogenes*. Artificial contamination is performed using a 10-fold dilution series in Ringer's solution (Oxoid) of a pure culture of *L. monocytogenes* EGDe containing $8.5 \times 10^8$ CFU/ml. 100 µl of the appropriate dilutions are added to the samples. The dilution series is prepared to contain $10^1$-$10^2$, $10^2$-$10^3$, $10^3$-$10^4$ and $10^4$-$10^5$ CFU/ml. The number of CFU for each step of the dilution series is obtained by the plate count method using tryptone soy agar with 0.6% yeast (TSA-Y; Oxoid). The experiment is performed in triplicates.

Naturally contaminated soft cheese samples are provided by regulatory authority and originated from a recent *L. monocytogenes* outbreak in Styria, Austria and are stored at 4° C. Two samples from two different production charges are processed in quadruplicates resulting in eight individual samples. Additionally, ISO 11290-2 is carried out accordingly for each sample to compare the quantitative results of the experiments with this standard method (ISO 11290-2; ISO 11290-2/Amd1).

1.9. Sample Treatment.

Sample treatment is performed using the matrix lysis protocol as published by Mester et al. (2010) J. Food Protect. 73, 680-687 and Rossmanith et al. (2007) J. Microbiol. Methods 69, 504-511.

1.10. Statistical analysis.

Two-group comparisons are analyzed by chi square test. P values are calculated, and values ≤0.05 are considered significant.

2. Application Examples 2.1. Phenotype of IAC+, Δ-prfA *L. monocytogenes* EGDe on OCLA, PALCAM, Blood Agar and RAPID' L.mono Agar Media.

On blood agar IAC+, Δ-prfA *L. monocytogenes* EGDe show no haemolysis. On PALCAM agar IAC+, Δ-prfA *L. monocytogenes* EGDe show the same phenotype as the *L. monocytogenes* EGDe wild type, as presented in Table 2. The morphology and colour of IAC+, Δ-prfA *L. monocytogenes* EGDe on OCLA is also similar to the wild type except the halo formation which is not observable for IAC+, Δ-prfA *L. monocytogenes* EGDe after 24 and 48 h of incubation. After 72 h of incubation IAC+, Δ-prfA *L. monocytogenes* EGDe show some weak halo formation as well. Plated on RAPID' L.mono the cloned strain develops white colour, lacking the characteristic green colour of the *L. monocytogenes* EGDe wild type strain on RAPID' L.mono agar.

TABLE 2

Colony morphology of the cloned *L. monocytogenes* EGDe ΔprfA, IAC+ strain in comparsion to the wild type *L. monocytogenes* EGDe and *L. innocua* on selected selective and chromogenic agar media.

| Strain/Media | | RAPID' L. mono | OCLA | PALCAM | Blood agar |
|---|---|---|---|---|---|
| *L. monocytogenes* EGDe Wildtype | Morphology | — | Halo formation[a] | Fish eye | — |
| | Colour | Green | Blue | Green | — |
| | Agar staining | no | — | Black | Haemolysis |
| *L. monocytogenes* EGDe ΔprfA, IAC+ | Morphology | — | Halo after 72 h[b] | Fish eye | — |
| | Colour | White | Blue | Green | — |
| | Agar staining | no | — | Black | No haem. |
| *L. innocua* | Morphology | — | No halo | Fish eye | — |
| | Colour | White | Blue | Green | — |
| | Agar staining | Yellow | — | Black | No haem. |

[a]Halo formation was finished after 24 h incubation at 37° C. for *L. monocytogenes* EGDe wildtype.
[b]No halo was observed for *L. monocytogenes* EGDe ΔprfA, IAC+ after 24 h and 48 h of incubation.

2.2. Application of IAC+, Δ-prfA *L. Monocytogenes* EGDe as Internal Process Control to Artificial Contaminated UHT Milk and Naturally Contaminated Quargel Cheese.

Artificially as well as naturally contaminated food samples are processed according to the method disclosed by Rossmanith et al. (2007) J. Microbiol. Methods 69, 504-511: This method is based on sample preparation by lysis of the food matrix and subsequent separation of the target bacteria using centrifugation followed by DNA isolation and real-time PCR detection. The ionic liquid 1-ethyl-3-methylimidazolium thiocyanate ([emim]SCN) is used as solvent during sample preparation.

For artificial contamination 12.5 g samples of UHT milk are spiked with a four-step decimal dilution series of *L. monocytogenes* EGDe wild type as described in section 1.8. Additionally, $1.4 \times 10^3$ (RSD.: 29.0%) CFU per sample of the internal sample process control IAC+, Δ-prfA *L. monocytogenes* EGDe are added.

The main target pathogen *L. monocytogenes* EGDe wild type is recovered from UHT milk by a factor of 55% (RSD (relative standard deviation): 10.9%) compared with microscopy count. The relative standard deviation within the log-scales is 10.9% representing a high level of precision and reproducibility in terms of log scale recovery and indicating no biasing influence of the internal sample process control by means of IAC+, Δ-prfA *L. monocytogenes* EGDe cells.

The internal sample process control indicates a recovery of 49% (RSD.: 27.1%) compared with microscopic count. Initially $1.4 \times 10^3$ (RSD.: 29.0%) CFU (colony forming unit) per sample results in $6.9 \times 10^2$ (RSD.: 27.0%) BCE after recovery and real-time PCR detection.

The system is then applied to naturally contaminated samples of Quargel cheese. Additionally $1.4 \times 10^3$ (RSD.: 29.0%) CFU IAC+, Δ-prfA *L. monocytogenes* EGDe are added per sample.

The samples are processed in two ways: A direct quantification of the value of *L. monocytogenes* is obtained by matrix lysis and subsequent real-time PCR. Also ISO 11290-2 is performed for comparison. Additionally the samples are processed by matrix lysis and subsequent real-time PCR using a DNA isolation protocol omitting the Proteinase K step. This artificially biases the digestion performance and resulting thereof the efficiency of the whole protocol.

The values of *L. monocytogenes* contamination of the samples directly obtained after real-time PCR reach an average of $1.4 \times 10^6$ (RSD.: 5.9%) BCE and $1.1 \times 10^8$ (RSD.: 8.9%) BCE for the two respective Quargel cheese charges. These values are corrected according to the rate of efficiency for each sample as obtained by comparing the values of each replicate to the average value of the IAC+, Δ-prfA *L. monocytogenes* EGDe process control of $6.9 \times 10^2$ (RSD.: 5.9%) BCE after real-time PCR. After this correction the *L. monocytogenes* contamination average $1.1 \times 10^6$ (RSD.: 35.8%) BCE and $2.3 \times 10^8$ (RSD.: 10.2%) for the two charges. A further correction including the overall loss of IAC+, Δ-prfA *L. monocytogenes* EGDe process control cells from initially $1.4 \times 10^3$ (RSD.: 29.0%) CFU to $6.9 \times 10^2$ (RSD.: 5.9%) BCE after real-time PCR is done. This results in $2.32 \times 10^6$ (RSD.: 36.0%) BCE/g and $5.0 \times 10^8$ (RSD.: 9.9%) BCE/g for the two cheese charges comparing to $2.07 \times 10^6$ (RSD.: 91.1%) CFU/g and $4.9 \times 10^8$ (RSD.: 73.2%) CFU/g as obtained by ISO 11290-2. The samples processed by artificially biased DNA isolation average in basic values of $4.9 \times 10^5$ (RSD.: 6.3%) BCE and $3.7 \times 10^7$ (RSD.: 2.9%) for the respective cheese charges. After correction as prescribed above the respective *L. monocytogenes* contamination is $1.8 \times 10^6$ (RSD.: 47%) BCE and $4.6 \times 10^8$ (RSD.: 10.1%) BCE.

The invention claimed is:

1. A genetically modified bacterium of the species *Listeria monocytogenes* comprising a deletion of the genomic locus of the transcriptional factor PrfA and further comprising, at the genomic level, an artificial sequence comprising the nucleic acid sequence of SEQ ID NO: 1 that acts as internal amplification control (IAC).

2. The *Listeria monocytogenes* bacterium of claim 1, wherein the artificial sequence that acts as IAC comprises primer binding sequences at the 5' and 3' ends.

3. The *Listeria monocytogenes* bacterium of claim 2, wherein the primer binding sequences are identical to the primer binding sequences of the genomic prfA locus of wild type *Listeria monocytogenes*.

4. A genetically modified *Listeria monocytogenes* EGDe strain of claim 1.

5. A genetically modified *Listeria monocytogenes* EGDe strain comprising a deletion of the genomic locus of the transcriptional factor PrfA and further comprising, at the genomic level, an integrated internal amplification control sequence (IAC) of SEQ ID NO: 1, which genetically modified strain has been deposited at the DSMZ as *Listeria monocytogenes* ΔprfA/+IAC under DSM 23639 on May 20, 2010.

6. A method for the qualitative or quantitative detection or determination of wild type *Listeria monocytogenes* in a sample suspected to be contaminated with said *Listeria monocytogenes*, comprising contacting said sample with the genetically modified *Listeria monocytogenes* of claim 1 and further processing the sample by (a) a first matrix lysis and subsequent real-time PCR to directly quantify a level of *L. monocytogenes* in said sample; (b) a second matrix lysis and subsequent real-time PCR using a DNA isolation protocol omitting the Proteinase K step to quantify a level of *L. monocytogenes* in said sample; and (c) optionally performing an ISO 11290-2 quantification for comparison.

7. The method according to claim 6, wherein the sample is a food sample.

8. The method according to claim 6, wherein the genetically modified *Listeria monocytogenes* of claim 1 is employed as internal sample process control (ISPC) for a real-time PCR based assay.

9. A method for detecting and determining the the presence or the amount of wild type *Listeria monocytogenes* in a sample suspected to be contaminated with said *Listeria monocytogenes*, comprising:

(a) adding to said sample a predefined amount of cells of the genetically modified *Listeria monocytogenes* bacterium of claim 1,
(b) incubating the sample with an extraction solution,
(c) isolating the DNA by standard methods;
(d) applying real-time PCR, thereby using
  (i) primers specific for the genomic prfA locus of wild type *Listeria monocytogenes* and the IAC sequence of genetically modified *Listeria monocytogenes* of claim 1; and
  (ii) a fluorescent labelled oligonucleotide probe that is able to specifically hybridize with said prfA locus and a fluorescent labelled oligonucleotide probe that is able to specifically hybridize with said IAC sequence,
(e) determining qualitatively or quantitatively fluorescent signals generated by step (d), and
(f) determining or calculating from step (e) the presence or the amount of the wild type *Listeria monocytogenes* cells in the original sample suspected to be contaminated with said *Listeria* monocytogenes micro organism.

10. The method according to claim 9, wherein the primers used in step (d)(i) are Lip1 (SEQ ID NO: 2) and Lip2 (SEQ ID NO: 3).

11. The method of claim 9, wherein the fluorescent labelled probes used in step (d)(ii) are pLucLm4 (SEQ ID NO: 4) for detecting the IAC sequence, and LipProbe (SEQ ID NO: 5) for detecting the prfA locus.

12. A method according to claim 9, wherein the extraction solution of step (b) comprises at least $MgCl_2$ or an ionic liquid.

13. A kit comprising, in one or more packages, (i) the genetically modified *Listeria monocytogenes* of claim 1;
(ii) the primers specific for the genomic prfA locus of wild type *Listeria monocytogenes* and the IAC sequence of the genetically modified *Listeria monocytogenes* of claim 1; and
(iii) a fluorescent labelled oligonucleotide probe that is able to specifically hybridize with said prfA locus and a fluorescent labelled oligonucleotide probe that is able to specifically hybridize with said IAC sequence.

14. The kit according to claim 13, wherein the primers are Lip1 (SEQ ID NO: 2) and Lip2 (SEQ ID NO: 3).

15. The kit according to claim 13, wherein the fluorescent labelled probes are pLucLm4 (SEQ ID NO: 4) for detecting the IAC sequence and LipProbe (SEQ ID NO: 5) for detecting the prfA locus.

16. A method for manufacturing a genetically modified *Listeria monocytogenes* bacterium of claim 1 comprising:

(a) deleting the genomic locus of the transcriptional factor PrfA of *Listeria monocytogenes,*
(b) cloning a vector comprising said IAC, and
(c) transforming the vector of step (b) into the *Listeria monocytogenes* d-PrfA strain of step (a).

* * * * *

UNITED STATES PATENT AND TRADEMARK OFFICE
CERTIFICATE OF CORRECTION

| | | |
|---|---|---|
| PATENT NO. | : 8,808,683 B2 | Page 1 of 1 |
| APPLICATION NO. | : 13/701142 | |
| DATED | : August 19, 2014 | |
| INVENTOR(S) | : Rossmanith et al. | |

It is certified that error appears in the above-identified patent and that said Letters Patent is hereby corrected as shown below:

In the Claims

Claim 9
Column 40, line 26 reads "with said *Listeria* monocytogenes micro organism"
should read -- with said *Listeria* monocytogenes --

Claim 16
Column 40, line 60 reads "*monocytogenes* d-PrfA strain of Step (a)."
should read -- *monocytogenes* δ-PrfA strain of Step (a). --

Signed and Sealed this
Twenty-sixth Day of May, 2015

Michelle K. Lee
*Director of the United States Patent and Trademark Office*

SEQUENCE LISTING

```
<160> NUMBER OF SEQ ID NOS: 17

<210> SEQ ID NO 1
<211> LENGTH: 100
<212> TYPE: DNA
<213> ORGANISM: Artificial Sequence
<220> FEATURE:
<223> OTHER INFORMATION: Description of Artificial Sequence: Synthetic
      Internal amplification control polynucleotide
<300> PUBLICATION INFORMATION:
<301> AUTHORS: ROSSMANITH ET AL.
<302> TITLE: DETECTION OF LISTERIA MONOCYTOGENESIN FOOD USING A COMBINED
      ENRICHEMENT/REAL-TIME PCR METHOD TARGETING THE PRFA GENE
<303> JOURNAL: RES. MICROBIOL.
<304> VOLUME: 157
<306> PAGES: 763-771
<307> DATE: 2006-04-03

<400> SEQUENCE: 1
gatacagaaa catcggttgg cgtattcgaa atgtccgttc ggttggcgct atgaagagat      60
acgcggtgga acctggaacc tgatggcatc aagattacac                          100

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer Lip1
<300> PUBLICATION INFORMATION:
<301> AUTHORS: D'AGOSTINO ET AL.
<302> TITLE: A VALIDATED PCR-BASED METHOD TO DETECT LISTERIA
```

```
        MONOCYTOGENES USING RAW MILF AS A FOOD MODEL TOWARDS
        AN INTERNATIONAL STANDARD
<303> JOURNAL: J. FOOD. PROT.
<304> VOLUME: 67
<306> PAGES: 1646-1655
<307> DATE: 2004

<400> SEQUENCE: 2
gatacagaaa catcggttgg c                                            21

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer Lip2
<300> PUBLICATION INFORMATION:
<301> AUTHORS: D'AGOSTINO ET AL.
<302> TITLE: A VALIDATED PCR-BASED METHOD TO DETECT LISTERIA
        MONOCYTOGENES USING RAW MILF AS A FOOD MODEL TOWARDS
        AN INTERNATIONAL STANDARD
<303> JOURNAL: J. FOOD PROT.
<304> VOLUME: 67
<306> PAGES: 1646-1655
<307> DATE: 2004

<400> SEQUENCE: 3
gtgtaatctt gatgccatca gg                                           22

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      pLucLm4: probe binding IAC
<300> PUBLICATION INFORMATION:
<301> AUTHORS: ROSSMANITH ET AL.
<302> TITLE: DETECTION OF LISTERIA MONOCYTOGENES IN FOOD USING A
        COMBINED ENRICHMENT/REAL-TIME PCR METHOD TARGETING
        THE PRFA GENE
<303> JOURNAL: RES. MICROBIOL.
<304> VOLUME: 157
<306> PAGES: 763-771
<307> DATE: 2006

<400> SEQUENCE: 4
ttcgaaatgt ccgttcggtt ggc                                          23

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      LipProbe: probe binding prfA locus
<300> PUBLICATION INFORMATION:
<301> AUTHORS: ROSSMANITH ET AL.
<302> TITLE: DETECTION OF LISTERIA MONOCYTOGENES IN FOOD USING A
        COMBINED ENRICHMENT/REAL-TIME PCR METHOD TARGETING
        THE PRFA GENE
<303> JOURNAL: RES. MICROBIOL.
<304> VOLUME: 157
<306> PAGES: 763-771

<400> SEQUENCE: 5
caggattaaa agttgaccgc a                                            21

<210> SEQ ID NO 6
<211> LENGTH: 31
```

```
<212> TYPE: DNA
<213> ORGANISM: Artificial Sequence
<220> FEATURE:
<223> OTHER INFORMATION: Description of Artificial Sequence: Synthetic
      LipBam primer

<400> SEQUENCE: 6
gcgcggatcc gatacagaaa catcggttgg c                                        31

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Synthetic
      LipSal primer

<400> SEQUENCE: 7
gcgcgtcgac gtgtaatctt gatgccatca gg                                       32

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gtcaaaacat acgctcttat c                                                   21

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
acataatcag tccaaagtag atgc                                                24

<210> SEQ ID NO 10
<211> LENGTH: 548
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(4)
<223> OTHER INFORMATION: a, c, t, g, unknown or other
<220> FEATURE:
<221> NAME/KEY: modified_base
<222> LOCATION: (6)..(8)
<223> OTHER INFORMATION: a, c, t, g, unknown or other

<400> SEQUENCE: 10
annnannnac gtatccagtt cgattcatgg accgagatga caacgaacta acagacctaa         60
cccaaacctt cccattaacg aagcgtaact aggtcaaaag acacccgaaa aagaaaaaat        120
gcataactta agaaaaacca ttgacaaaca agcgatttaa acataaaatg gtatttggct        180
gttgaaaaga cagtgccatt tgtcctgata gctcagctgg atagagcaac ggccttctaa        240
gccgtcggtc gggggttcga atccctctca ggacgttaaa tagtaatgta aagaaatctc        300
taaaacgttg aaaagccttg atattaaagg gcggatgaat gttttggagt ttttttttata      360
```

```
tcgtataata cccgttttat tccgttgttt ttgtggcatt tgtggtaaaa tttgtggtat    420
tttcatctgt ttttagtgtg aaaaaagcat ctactttgga ctgattatgg taaaaccacc    480
aacttggaat ggataaggtc atctccattg gagagagtat gtgcacccac tacttacgga    540
tgatttag                                                             548
```

<210> SEQ ID NO 11
<211> LENGTH: 550
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (3)..(5)
<223> OTHER INFORMATION: a, c, t, g, unknown or other
<220> FEATURE:
<221> NAME/KEY: modified_base
<222> LOCATION: (13)..(14)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: modified_base
<222> LOCATION: (528)..(528)
<223> OTHER INFORMATION: a, c, t, g, unknown or other

<400> SEQUENCE: 11

```
ggnnntgaaa cgnncnagtt cgattcatgg accgagatga caacgaacta acagacctaa     60
cccaaacctt cccattaacg aagcgtaact aggtcaaaag cacccgaaa aagaaaaaat    120 gcaataactt aaagaaaacc attgacaaac aagcgattta aacataaaat ggtatttggc    180
tgttgaaaag acagtgccat ttgtcctgat agctcagctg gatagagcaa cggccttcta    240
agccgtcggt cggggttcg aatccctctc aggacgttaa atagtaatgt aaagaaatct    300
ctaaaacgtt gaaaagcctt gatattaaag ggcggatgaa tgttttggag ttttttttat    360
atcgtataat acccgtttta ttccgttgtt tttgtggcat ttgtggtaaa atttgtggta    420
ttttcatctg ttttagtgt gaaaaaagca tctactttgg actgattatg gtaaaaacaa    480
cctacttggg atggttaagg gcacatccat tggagagagt atgtgtancc tctttggagg    540
actgatgagg                                                           550
```

<210> SEQ ID NO 12
<211> LENGTH: 605
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (5)..(7)
<223> OTHER INFORMATION: a, c, t, g, unknown or other

<400> SEQUENCE: 12

```
nnaannngta tccagttcga ttcatggacc gagatgacaa cgaactaaca gacctaaccc     60
aaaccttccc attaacgaag cgtaactagg tcaaaagaca cccgaaaaag aaaaaatgca    120
```

| | |
|---|---|
| ataacttaaa gaaaaccatt gacaaacaag cgatttaaac ataaaatggt atttggctgt | 180 |
| tgaaaagaca gtgccatttg tcctgatagc tcagctggat agagcaacgg ccttctaagc | 240 |
| cgtcggtcgg gggttcgaat ccctctcagg acgttaaata gtaatgtaaa gaaatctcta | 300 |
| aaacgttgaa aagccttgat attaaagggc ggatgaatgt tttggagttt ttttttatatc | 360 |
| gtataatacc cgttttattc cgttgttttt gtggcatttg tggtaaaatt tgtggtatttt | 420 |
| tcatctgttt ttagtgtgaa aaagcatct actttggctg attatggtaa atccacctac | 480 |
| tttgaatgga taaggtcatc tccattggag agagtatgtg tatctacttt gtagggatga | 540 |
| tgatgtacca cctaggttgg actgaatagg tcccccttc ttcgattaaa caacgggata | 600 |
| aagta | 605 |

<210> SEQ ID NO 13
<211> LENGTH: 550
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: modified_base
<222> LOCATION: (6)..(7)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other

<400> SEQUENCE: 13

| | |
|---|---|
| nnnntnncna agtatccagt tcgattcatg gaccgagatg acacgaacta acagacctaa | 60 |
| cccaaacctt cccattaacg aagcgtaact aggtcaaaag acacccgaaa agaaaaaat | 120 |
| gcaataactt aaagaaaacc attgacaaac aagcgattta acataaaat ggtatttggc | 180 |
| tgttgaaaag acagtgccat tgtcctgat agctcagctg gatagagcaa cggccttcta | 240 |
| agccgtcggt cggggggttcg aatccctctc aggacgttaa atagtaatgt aaagaaatct | 300 |
| ctaaaacgtt gaaaagcctt gatattaaag ggcggatgaa tgttttggag ttttttttat | 360 |
| atcgtataat acccgtttta ttccgttgtt tttgtggcat ttgtggtaaa atttgtggta | 420 |
| ttttcatctg ttttagtgt gaaaaagca tctactttgg actgattatg taaaacaacc | 480 |
| tactttggat ggattaggta atatcttttt gacagagtat gtgtaccatc tttttaggac | 540 |
| tgattatgta | 550 |

<210> SEQ ID NO 14
<211> LENGTH: 498
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: modified_base
<222> LOCATION: (6)..(7)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 14

```
nnnnannaaa aacgnatgaa ataccacaaa ttttaccaca aatgccacaa aaacaacgga      60
ataaaacggg tattatacga tataaaaaaa actccaaaac attcatccgc cctttaatat     120
caaggctttt caacgtttta aagatttctt tacattacta tttaacgtcc tgagagggat     180
tcgaaccccc gaccgacggc ttaaaaggcc gttgctctat ccagctgagc tatcaggaca     240
aatggcactg tcttttcaac agccaaatac catttatgt ttaaatcgct tgtttgtcaa      300
tggttttctt taagttattg cattttttct ttttcgggtg tcttttgacc tatttacgct     360
tcgttaatgg gaaggtttgg gttaggtctg ttagttcgtt gtcatctcgg tccatgaatc     420
gaacttggat accttctggt gttgaatcga taagagcgta tgttttgaac aaccacctac     480
tttggactga ttaggtaa                                                   498
```

<210> SEQ ID NO 15
<211> LENGTH: 606
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (2)..(3)
<223> OTHER INFORMATION: a, c, t, g, unknown or other
<220> FEATURE:
<221> NAME/KEY: modified_base
<222> LOCATION: (5)..(6)
<223> OTHER INFORMATION: a, c, t, g, unknown or other
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (454)..(455)
<223> OTHER INFORMATION: a, c, t, g, unknown or other
<220> FEATURE:
<221> NAME/KEY: modified_base
<222> LOCATION: (467)..(467)
<223> OTHER INFORMATION: a, c, t, g, unknown or other
<220> FEATURE:
<221> NAME/KEY: modified_base
<222> LOCATION: (529)..(529)
<223> OTHER INFORMATION: a, c, t, g, unknown or other
<220> FEATURE:
<221> NAME/KEY: modified_base
<222> LOCATION: (606)..(606)
<223> OTHER INFORMATION: a, c, t, g, unknown or other

<400> SEQUENCE: 15

```
tnntnnanac gatgacatac cacaaatttt accacaaatg ccacaaaaac aacggaataa      60
aacgggtatt atacgatata aaaaaaactc caaaacattc atccgccctt taatatcaag     120
gcttttcaac gttttaaaga tttctttaca ttactatttta acgtcctgag agggattcga     180 accccgacc gacggcttaa aaggccgttg ctctatccag ctgagctatc aggacaaatg      240
gcactgtctt tcaacagcc aaataccatt ttatgtttaa atcgcttgtt tgtcaatggt     300
tttctttaag ttattgcatt ttttcttttt cgggtgtctt ttgacctagt tacgcttcgt     360
taatgggaag gtttgggtta ggtctgttag ttcgttgtca tctcggtcca tgaatcgaac     420
ttggatacct tctggtgttg aatcgataag agcnntggtt tttgtanaca aaaccttta     480 ctttggactg aataaggtac cccccttgt aaaggtttta tgtgaaccnc ctttgtagag     540
```

```
ttaatttgga accaccgagg ggggattgat taggccaccc tgcctttaag ttcaggtggg     600 cgacan                                                                606
```

<210> SEQ ID NO 16
<211> LENGTH: 551
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (551)..(551)
<223> OTHER INFORMATION: a, c, t, g, unknown or other

<400> SEQUENCE: 16

```
nnttagntaa aacgatgaaa taccacaaat tttaccacaa atgccacaaa aacaacggaa     60
taaaacgggt attatacgat ataaaaaaaa ctccaaaaca ttcatccgcc ctttaatatc    120
aaggcttttc aacgttttaa agatttcttt acattactat ttaacgtcct gagagggatt    180 cgaaccccg accgacggct taaaaggccg ttgctctatc cagctgagct atcaggacaa    240
atggcactgt cttttcaaca gccaaatacc attttatgtt taaatcgctt gtttgtcaat    300
ggttttcttt aagttattgc atttttctt tttcgggtgt cttttgacct agttacgctt    360
cgttaatggg aaggtttggg ttaggtctgt tagttcgttg tcatctcggt ccatgaatcg    420
aacttggata ccttctggtg ttgaatcgat aagagcgtat gttttgacc aaccatcaac    480 tttggacgga ttaggtaacc tccatttgag agagtatatg taacacctat tttgggaggt    540
atgatgaaaa n                                                         551
```

<210> SEQ ID NO 17
<211> LENGTH: 514
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(5)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 17

```
tnnnngtana aangatgaaa taccacaaat tttaccacaa atgccacaaa aacaacggaa     60
taaaacgggt attatacgat ataaaaaaaa ctccaaaaca ttcatccgcc ctttaatatc    120
aaggcttttc aacgttttag agatttcttt acattactat ttaacgtcct gagagggatt    180 cgaaccccg accgacggct taaaaggccg ttgctctatc cagctgagct atcaggacaa    240
```

```
atggcactgt cttttcaaca gccaaatacc attttatgtt taaatcgctt gtttgtcaat    300
ggttttcttt aagttattgc atttttctt tttcgggtgt cttttgacct agttacgctt    360
cgttaatggg aaggtttggg ttaggtctgt tagttcgttg tcatctcggt ccatgaatcg    420
aacttggata ccttctggtg ttgaatcgat aaaagcgtat gttttgaaaa accatcaact    480
ttgaacggat taggtaacct ccattttgga gaga                                514
```